(12) United States Patent
Inoue et al.

(10) Patent No.: US 7,993,494 B2
(45) Date of Patent: Aug. 9, 2011

(54) METHOD FOR MANUFACTURING TRIARYLPYRAZINE DERIVATIVE

(75) Inventors: Hideko Inoue, Kanagawa (JP); Hiroko Nomura, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 381 days.

(21) Appl. No.: 12/354,403

(22) Filed: Jan. 15, 2009

(65) Prior Publication Data
US 2009/0183982 A1  Jul. 23, 2009

(30) Foreign Application Priority Data

Jan. 23, 2008  (JP) ................................ 2008-012468

(51) Int. Cl.
*B01J 19/12* (2006.01)
*C07C 209/68* (2006.01)
*C07D 213/61* (2006.01)
*C09K 11/06* (2006.01)

(52) U.S. Cl. ......... 204/157.72; 204/157.86; 204/157.85; 204/157.81; 204/157.82; 252/301.16

(58) Field of Classification Search ............. 204/157.72, 204/157.81, 157.82, 157.85, 157.86; 514/85; 252/301.16
See application file for complete search history.

(56) References Cited

U.S. PATENT DOCUMENTS

| | | | | |
|---|---|---|---|---|
| 4,097,478 A | * | 6/1978 | Sato | 544/353 |
| 4,303,689 A | * | 12/1981 | Winter et al. | 426/537 |
| 6,821,646 B2 | | 11/2004 | Tsuboyama et al. | |
| 7,220,495 B2 | | 5/2007 | Tsuboyama et al. | |
| 2003/0059646 A1 | | 3/2003 | Kamatani et al. | |
| 2005/0221123 A1 | | 10/2005 | Inoue et al. | |
| 2005/0253135 A1 | | 11/2005 | Stossel et al. | |
| 2006/0127696 A1 | | 6/2006 | Stossel et al. | |
| 2007/0129545 A1 | | 6/2007 | Inoue et al. | |
| 2007/0244320 A1 | | 10/2007 | Inoue et al. | |

FOREIGN PATENT DOCUMENTS

| | | | |
|---|---|---|---|
| JP | 49101391 A | * | 9/1974 |
| JP | 63162678 A | * | 7/1988 |
| JP | 2002-105055 | | 4/2002 |
| JP | 2007-284432 | | 11/2007 |
| WO | WO 2005/115061 A1 | | 12/2005 |

(Continued)

OTHER PUBLICATIONS

Tsutsui,T. et al., "High Quantum Efficiency in Organic Light-Emitting Devices with Iridium-Complex as a Triplet Emissive Center," Jpn. J. Appl. Phys., (Japanese Journal of Applied Physics), vol. 38/Part 2, No. 12 B, Dec. 15, 1999, pp. L1502-L1504.

(Continued)

*Primary Examiner* — Nam X Nguyen
*Assistant Examiner* — Colleen M Raphael
(74) *Attorney, Agent, or Firm* — Husch Blackwell LLP

(57) ABSTRACT

A novel synthesis method of a triarylpyrazine derivative, in particular, a manufacturing method by which a triarylpyrazine derivative, in specific, a 2,3,5-triarylpyrazine derivative in which an aryl group at a 5-position includes a substituent having an electron-withdrawing property can be synthesized with high yield as compared to a conventional method is provided. By using a synthesis method in which a mixture including a 1-aryl-2-(methylsulfinyl)ethanone derivative, meso-1,2-diarylethylenediamine, and a dehydrogenation agent is irradiated with a microwave to be reacted, the above object is achieved.

21 Claims, 6 Drawing Sheets

FOREIGN PATENT DOCUMENTS

WO WO 2006/098460 A1 9/2006

OTHER PUBLICATIONS

O'Brien, D. et al., "Improved Energy Transfer in Electrophosphorescent Devices," Appl. Phys. Lett., (Applied Physics Letters), vol. 74, No. 3, Jan. 18, 1999, pp. 442-444.

Baldo, M. et al., "High-Efficiency Fluorescent Organic Light-Emitting Devices Using a Phosphorescent Sensitizer," Nature, vol. 403, Feb. 17, 2000, pp. 750-753.

Thompson, M. et al., "Phosphorescent Materials and Devices," Proceedings of the 10th International Workshop on Inorganic and Organic Electroluminescence (EL'00), Dec. 4, 2000, pp. 35-38.

Duan, J. et al., "New Iridium Complexes as Highly Efficient Orange-Red Emitters in Organic Light-Emitting Diodes," Adv. Mater. (Advanced Materials), vol. 15, No. 3, Feb. 5, 2003, pp. 224-228.

Zhang, L. et al., "Synthesis and Phosphorescence of a New Iridium(III) Pyrazine Complex," Wuli Huaxue Xuebao (Acta Phys.-Chimica Sinica), vol. 19, No. 10, Oct. 19, 2003, pp. 889-891 (with English Abstract).

Zhang, L. et al., "Synthesis and Luminescence Property of a New Yellow Phosohorescent Iridium(III) Pyrazine Complex," Chemical Journal of Chinese Universities, vol. 25, No. 3, Mar. 1, 2004, pp. 397-400 (with English Abstract).

\* cited by examiner

METHOD FOR MANUFACTURING TRIARYLPYRAZINE DERIVATIVE

BACKGROUND OF THE INVENTION

1. Field of the Invention

The present invention relates to a method for manufacturing a triarylpyrazine derivative. In particular, the present invention relates to a method for manufacturing a 2,3,5-triarylpyrazine derivative in which a substituent having an electron-withdrawing property is bound to an aryl group at a 5-position.

2. Description of the Related Art

A display device using a light-emitting element in which an organic compound is used as a light-emitting substance (organic EL element) has been developed rapidly as a next generation display device because it has advantages such as thinness, lightness in weight, high response speed, and low power consumption. Although there have been various obstacles, technique has been improved such that organic EL televisions have become commercially available recently.

In an organic EL element, when voltage is applied between a pair of electrodes which interpose a light-emitting layer, electrons and holes injected from the electrodes are recombined to form an excited state, and when the excited state returns to a ground state, light is emitted. A wavelength of light emitted from a light-emitting substance is peculiar to the light-emitting substance; thus, by using different types of organic compounds as light-emitting substances, light-emitting elements which exhibit various wavelengths, i.e., various colors can be obtained.

In a case of a display device which is expected to display images, such as a display, at least three colors of light, i.e., red, green, and blue are required to be obtained in order to reproduce full-color images. To achieve this, for example, there are following methods: a method in which a light-emitting element emitting light with a light-emitting spectrum in a wide wavelength and a color filter are combined, a method in which a light-emitting element emitting light with a shorter wavelength than a wavelength of an objective color and a color conversion layer are combined, a method in which a light-emitting element emitting light with a desired wavelength is used. Among these three methods, the final one, i.e., a method in which a desired wavelength is obtained directly is preferable because loss in energy is small if the method is used.

This method is adapted to the above-described organic EL televisions which have become commercially available; however, actually, in addition to that method, a color filter is used, and a micro cavity structure is used for a light-emitting element in order to improve color purity. Organic EL televisions have got many advantages but is naturally expected to provide high quality images as a next generation television, and a light-emitting element exhibiting an appropriate emission color is required to live up to the expectation.

A light emitted from a light-emitting substance is peculiar to the substance as described above. There are many measures to improve the color purity of the organic EL television, which means that a light-emitting element which exhibits light emission of a favorable color and also satisfies another components such as a lifetime or power consumption is very difficult to be obtained. In addition, important characteristics of a light-emitting element, such as a lifetime or power consumption, do not necessarily depend on only a substance exhibiting light emission. The characteristics are affected also by layers other than a light-emitting layer, an element structure, an affinity between a light-emitting substance and a host, or the like. Therefore, there is no doubt that many kinds of light-emitting substances exhibiting light emission of a favorable color are needed to show the growth of this field.

In any case, there are not many light-emitting substances exhibiting light emission of a favorable color which is sufficient for productization in the present situation. In view of this present situation, an organometallic complex as shown in Patent Document 1 is proposed as one of substances exhibiting a favorable red light emission (Patent Document 1) from the present applicant.

In this Patent Document 1, it is disclosed that an organometallic complex in which a pyrazine derivative is used as a ligand exhibits a favorable red light. In general, a pyrazine derivative can be obtained by dehydration condensation of α-diketone and diamine, and an oxidative dehydrogenation reaction following the dehydration condensation.

[Patent Document 1] Japanese Published Patent Application No. 2007-284432.

SUMMARY OF THE INVENTION

However, the number of kinds of pyrazine derivatives that can be synthesized through this reaction is not so large, and the number of examples of arylpyrazine is even smaller. In particular, the present inventors found that a triarylpyrazine derivative including a substituted aryl group at a 5-position is very difficult to be synthesized through this reaction. Further, in a case where this substituent is a substituent having an electron-withdrawing property, the triarylpyrazine derivative is very difficult to be synthesized.

Therefore, in the present invention, it is an object to provide a novel synthesis method of a triarylpyrazine derivative. In particular, it is an object to provide a synthesis method by which a triarylpyrazine derivative, in specific, a 2,3,5-triarylpyrazine derivative in which an aryl group at a 5-position is an aryl group which includes a substituent having an electron-withdrawing property can be synthesized with high yield as compared to a conventional method.

As a result of diligent studies, the present inventors have found that a triarylpyrazine derivative represented by a following general formula (G1) can be obtained with high yield, in which an aryl group ($Ar^1$) bound to a 5-position includes a substituent having an electron-withdrawing property, by a synthesis method in which a mixture including a 1-aryl-2-(methylsulfinyl)ethanone derivative represented by a following general formula (M1), meso-1,2-diarylethylenediamine represented by a following general formula (M2), and a dehydrogenation agent is irradiated with a microwave to be reacted.

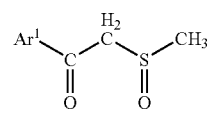

(M1)

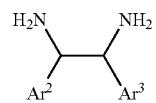

(M2)

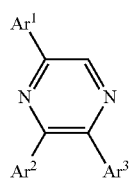
(G1)

In the formulae, $Ar^2$ and $Ar^3$ each independently represent a substituted or unsubstituted aryl group having 6 to 14 carbon atoms.

One aspect of the present invention is a method for manufacturing a triarylpyrazine derivative, in which a mixture including a material 1 represented by the following general formula (M1), a material 2 represented by the following general formula (M2), and a dehydrogenation agent is irradiated with a microwave to be reacted to produce a triarylpyrazine represented by the following general formula (G1).

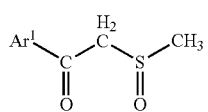
(M1)

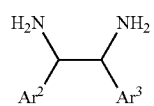
(M2)

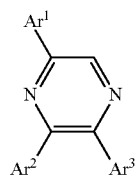
(G1)

In the formulae, $Ar^1$ represents an aryl group having 6 to 14 carbon atoms which includes at least one electron-withdrawing group, and $Ar^2$ and $Ar^3$ each independently represent a substituted or unsubstituted aryl group having 6 to 14 carbon atoms.

Another aspect of the present invention is a method for manufacturing a triarylpyrazine derivative, in which a mixture including a material 1 represented by a following general formula (M3), a material 2 represented by the following general formula (M2), and a dehydrogenation agent is irradiated with a microwave to be reacted to produce triarylpyrazine represented by a following general formula (G2).

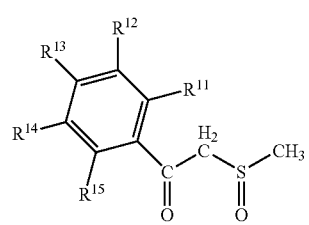
(M3)

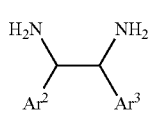
(M2)

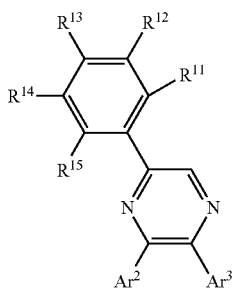
(G2)

In the formulae, $R^{11}$ to $R^{15}$ each independently represent hydrogen or an electron-withdrawing group, and at least one of $R^{11}$ to $R^{15}$ is an electron-withdrawing group, and further, $Ar^2$ and $Ar^3$ each independently represent a substituted or unsubstituted aryl group having 6 to 14 carbon atoms.

Another aspect of the present invention is a method for manufacturing a triarylpyrazine derivative in which a mixture including a material 1 represented by the following general formula (M3), a material 2 represented by a following structural formula (M5), and a dehydrogenation agent is irradiated with a microwave to be reacted to produce triarylpyrazine represented by a following general formula (G3).

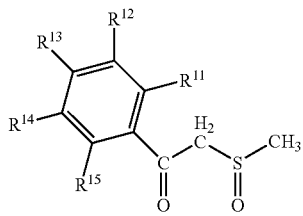
(M3)

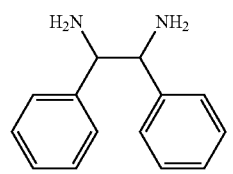
(M5)

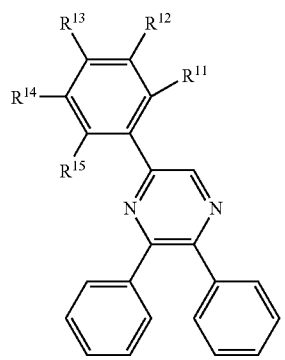
(G3)

In the formulae, $R^{11}$ to $R^5$ each independently represent hydrogen or an electron-withdrawing group, and at least one of $R^{11}$ to $R^{15}$ is an electron-withdrawing group.

Another aspect of the present invention is a method for manufacturing a triarylpyrazine derivative in which a mixture including a material 1 represented by a following general formula (M6), a material 2 represented by the following structural formula (M5), and a dehydrogenation agent is irradiated with a microwave to be reacted to produce triarylpyrazine represented by a following general formula (G4).

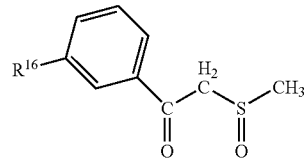
(M6)

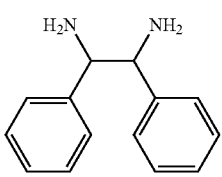
(M5)

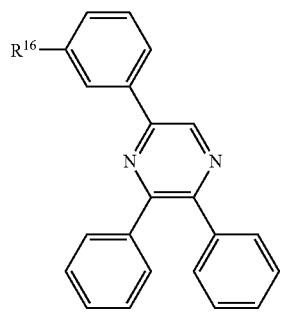
(G4)

In the formulae, $R^{16}$ represents an electron-withdrawing group.

Another aspect of the present invention is a method for manufacturing a triarylpyrazine derivative in which a mixture including a material 1 represented by a following general formula (M7), a material 2 represented by the following structural formula (M5), and a dehydrogenation agent is irradiated with a microwave to be reacted to produce triarylpyrazine represented by a following general formula (G5).

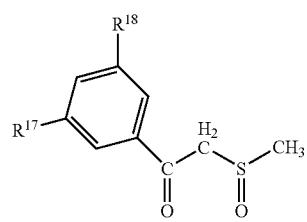
(M7)

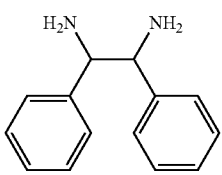
(M5)

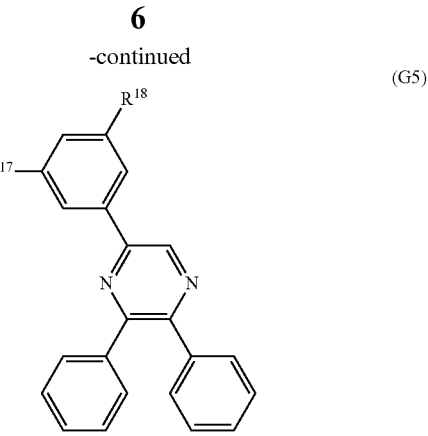
(G5)

In the formulae, $R^{17}$ and $R^{18}$ each independently represent an electron-withdrawing group.

Note that, as an example of an electron-withdrawing group, a halogen group such as a fluoro group; a haloalkyl group such as a trifluoromethyl group; a cyano group; an alkoxy group; a nitro group; or the like can be given.

Another aspect of the present invention is a method for manufacturing a triphenylpyrazine derivative in which a mixture including 1-(3-fluorophenyl)-2-(methylsulfinyl)ethanone (material 1) represented by a following structural formula (M8), meso-1,2-diphenylethylenediamine (material 2) represented by the following structural formula (M5), and a dehydrogenation agent is irradiated with a microwave to be reacted to produce 5-(3-fluorophenyl)-2,3-diphenylpyrazine represented by a following structural formula (1).

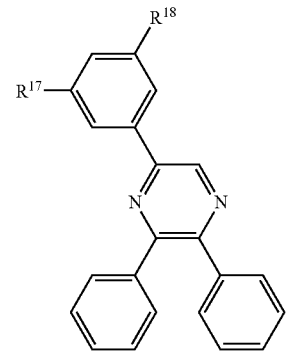
(M8)

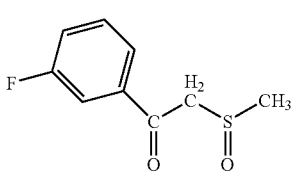
(M5)

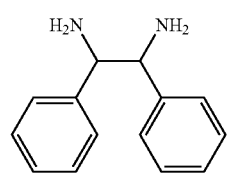

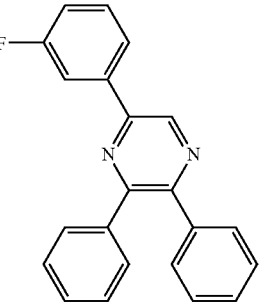
(1)

Another aspect of the present invention is a method for manufacturing a triphenylpyrazine derivative in which a mixture including 1-(3,5-difluorophenyl)-2-(methylsulfinyl) ethanone (material 1) represented by a following structural formula (M9), meso-1,2-diphenylethylenediamine (material 2) represented by the following structural formula (M5), and a dehydrogenation agent is irradiated with a microwave to be reacted to produce 5-(3,5-difluorophenyl)-2,3-diphenylpyrazine represented by a following structural formula (2).

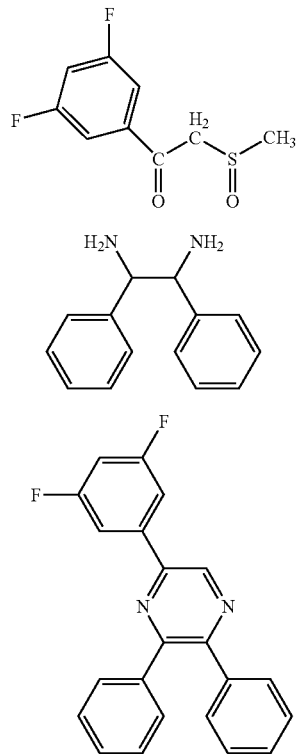

Note that, in the present invention, it is preferable that the mixture including the material 1, the material 2, and the dehydrogenation agent further includes an organic solvent, which makes the progress of a reaction easier. More preferably, the organic solvent has a polarity because heating with a microwave is performed effectively.

Further, as the above dehydrogenation agent, iron(III) chloride, sulfur, sodium hydroxide, a chloranil-based oxidizer, or the like can be used.

By a synthesis method of the present invention, a 2,3,5-triarylpyrazine derivative in which an aryl group at a 5-position includes a substituent having an electron-withdrawing property can be synthesized easily. In addition, the triarylpyrazine derivative can be synthesized with high yield.

DETAILED DESCRIPTION OF THE INVENTION

Figure 1A:
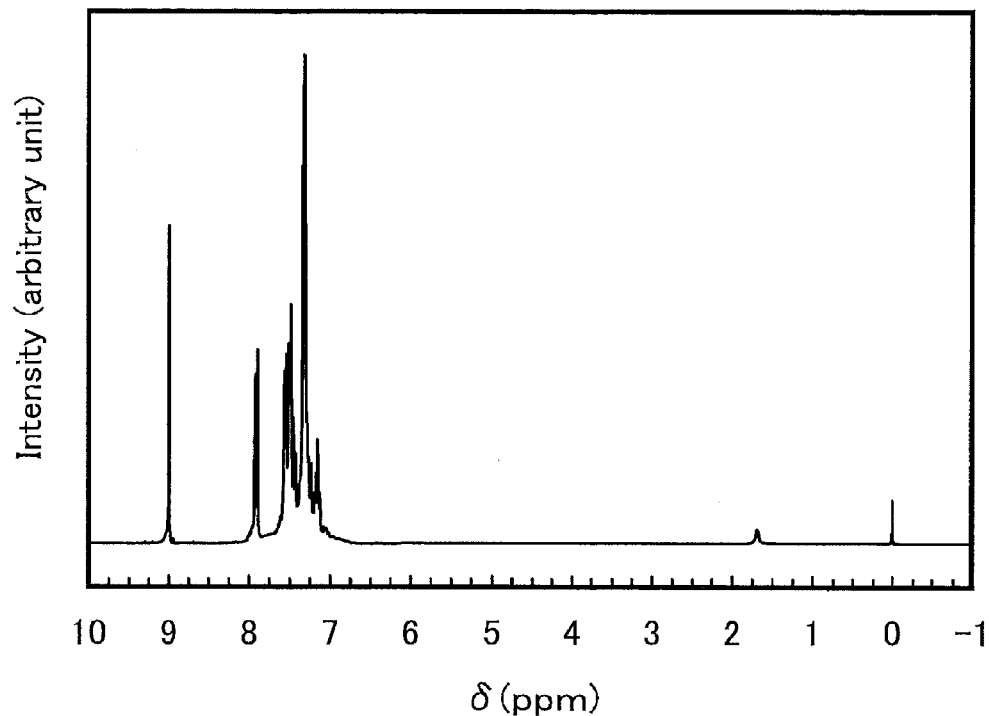
FIGS. 1A and 1B are NMR charts of 5-(3-fluorophenyl)-2,3-diphenylpyrazine which was synthesized in Synthesis Example 1 in Embodiment 1.

Hereinafter, embodiment modes of the present invention are described. However, the present invention can be carried out in many different modes, and it is easily understood by those skilled in the art that the mode and detail can be variously changed without departing from the spirit and scope of the present invention. Therefore, the present invention is not interpreted as being limited to the following description of the embodiment modes.

Embodiment Mode 1

In the present invention, as represented by a following scheme (a), a 1-aryl-2-(methylsulfinyl)ethanone derivative represented by the general formula (M1) and meso-1,2-diarylethylenediamine represented by the general formula (M2) are mixed with a dehydrogenation agent to be irradiated with a microwave, so that a triarylpyrazine derivative represented by the general formula (G1) can be obtained. In this case, it is preferable to use a solvent because the progress of reaction can be easier.

In general, as for a microwave, a microwave with a frequency of 2.45 GHz is used, and irradiation is performed with an output in the range of 0 to 200 W. A reaction temperature is preferably higher than or equal to 50° C. and lower than or equal to 120° C., and an output of a microwave is decided so as to be in the range. Further, output of a microwave is also controlled by a reaction pressure. A reaction temperature and a reaction pressure can also be controlled by whether irradiation is continuously performed with a microwave or irradiation is intermittently performed with a microwave. In a case where a solvent is used, a reaction temperature is set so as to be lower than or equal to a boiling point of the solvent. Further, a reaction pressure may be decided as appropriate depending on how easily the solvent is volatilized. A reaction time is adjusted with the state of the generation of product.

There is no particular limitation on a dehydrogenation agent which is used. For example, iron(III) chloride, sulfur, sodium hydroxide, a chloranil-based oxidizer, or the like can be used. The chloranil-based oxidizer corresponds to a substance in which benzoquinone is substituted by plurality of electron-withdrawing groups. For example, 2,3,5,6-tetrachloro-p-benzoquinone (commonly called: chloranil), 2,3-dichloro-5,6-dicyano-p-benzoquinone (abbreviation: DDQ), or the like can be given.

In a case where a solvent is used, there is no particular limitation on a solvent which is used. For example, an organic solvent such as methanol, ethanol, 2-ethoxyethanol, dimethylsulfoxide, or acetonitrile can be used. There is also no particular limitation on polarity of the solvent, so either a polar solvent or a nonpolar solvent can be used. However, a polar solvent is preferably used, and in particular, a solvent which includes a certain dielectric constant (dielectric constant of about greater than or equal to 10 and less than or equal to 50) is preferable because heat treatment with a microwave functions effectively if the solvent is used.

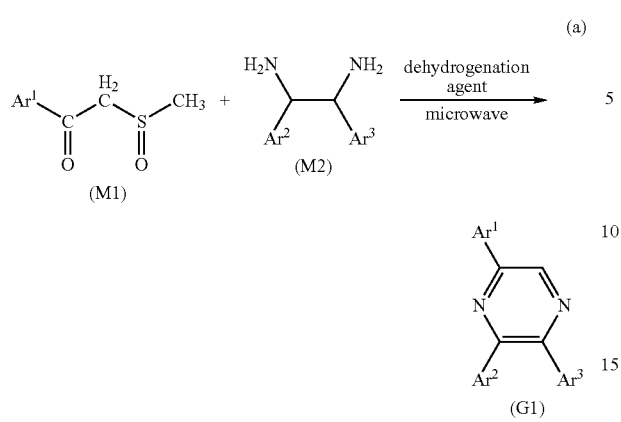

(a)

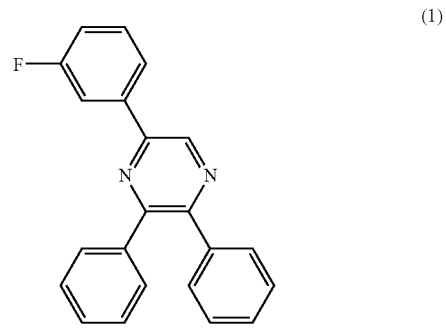

(1)

In the formula, $Ar^1$ represents an aryl group having 6 to 14 carbon atoms which includes at least one electron-withdrawing group, and $Ar^2$ and $Ar^3$ each independently represent a substituted or unsubstituted aryl group having 6 to 14 carbon atoms.

A substituent represented by $Ar^1$ is an aryl group having 6 to 14 carbon atoms. Specifically, a phenyl group, a naphthyl group, an anthryl group, or the like can be given. $Ar^1$ includes at least one substituent, and at least one of the substituents is a substituent having an electron-withdrawing property. As the substituent having an electron-withdrawing property, a halogen group such as a fluoro group; a haloalkyl group such as a trifluoromethyl group; a cyano group; a methoxy group; an alkoxy group such as an ethoxy group; a nitro group; or the like can be given. By the above synthesis method, a target substance can be obtained with high yield even in a case where $Ar^1$ includes a substituent having an electron-withdrawing property.

$Ar^2$ and $Ar^3$ each independently represent a substituted or unsubstituted aryl group having 6 to 14 carbon atoms. As the aryl group having 6 to 14 carbon atoms, specifically, a phenyl group, a naphthyl group, an anthryl group, or the like can be given. In a case where the aryl group includes a substituent, an alkoxy group, an alkoxycarbonyl group, a carboxy group, a halogen group, or the like can be given as the substituent.

A substituent represented by $Ar^1$ is an aryl group having 6 to 14 carbon atoms. Specifically, a phenyl group, a naphthyl group, an anthryl group, or the like can be given. $Ar^1$ includes at least one substituent, and at least one of the substituents is a substituent having an electron-withdrawing property. As the substituent having an electron-withdrawing property, a halogen group such as a fluoro group; a haloalkyl group such as a trifluoromethyl group; a cyano group; an alkoxy group such as a methoxy group and an ethoxy group; a nitro group; or the like can be given. By the above synthesis method, a target substance can be obtained with high yield even in a case where $Ar^1$ includes a substituent having an electron-withdrawing property.

By the above synthesis method, a 2,3,5-triarylpyrazine derivative in which a substituent having an electron-withdrawing property is attached to an aryl group bound to a 5-position, for example, 5-(3-fluorophenyl)-2,3-diphenylpyrazine (abbreviation: Hdppr-3FP) represented by the following structural formula (1) can be synthesized with high yield.

Note that a synthesis method of 1-aryl-2-(methylsulfinyl) ethanone represented by the general formula (M1), which is used in the reaction formula represented by the above scheme (a), is described. As in the following scheme (b), 1-aryl-2-(methylsulfinyl)ethanone can be obtained as follows: sodium hydride and dimethylsulfoxide are heated while being stirred to be reacted, and then the reaction product is reacted with aromatic carboxylic acid ester.

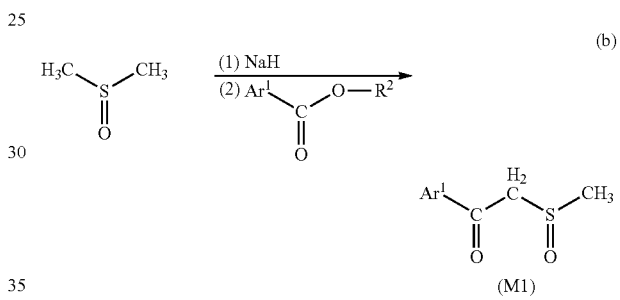

(b)

Embodiment 1

Synthesis Example 1

In this synthesis example, a synthesis method of 5-(3-fluorophenyl)-2,3-diphenylpyrazine (abbreviation: Hdppr-3FP) which is an arylpyrazine derivative represented by the structural formula (1) in Embodiment Mode 1 is described.

Step 1: Synthesis of Intermediate, 1-(3-fluorophenyl)-2-(methylsulfinyl)ethanone First, to a three-necked flask was placed 7.85 g of 60% sodium hydride (oily), and was added 50 mL of petroleum ether to be stirred for 1 minute. After the solution is left still, the supernatant fluid was discarded. After this washing operation of sodium hydride with petroleum ether was repeated three times, sodium hydride was dried under reduced pressure. After drying, to sodium hydride was added dropwise 80 mL of dimethylsulfoxide. The mixture was stirred while being heated at 70° C. for 1 hour to be reacted. After the reaction, the reaction mixture was cooled down to room temperature. This mixture was cooled with ice, and 10 g of m-fluoroethyl benzoate was added dropwise to the mixture with a syringe. This mixture was stirred at room temperature for 15 hours to be reacted. After the reaction, to this mixture were added a small amount of ethanol and pure water in this order. This mixture was added to 300 mL of water to be stirred, and this solution was adjusted so that pH thereof is 3 with 1 M dilute hydrochloric acid. To this solution was added chloroform, and an organic layer was extracted. After extracting, the organic layer was washed with a saturated aqueous sodium chloride solution three times. After washing, magnesium sulfate was added to the organic layer to dry the organic layer. After drying, this mixture was subjected to suction filtration to obtain a filtrate. The obtained filtrate was concentrated and recrystallized with a mixed solvent of ethyl acetate and hexane. Thus, an intermediate, 1-(3-fluorophenyl)-2-(methylsulfinyl)ethanone (a light brown solid, yield: 42%) was obtained. A synthetic scheme of Step 1 is shown by a following (a-1).

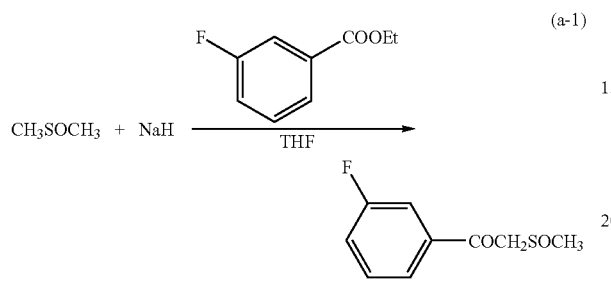

(a-1)

Step 2: Synthesis of 5-(3-fluorophenyl)-2,3-diphenylpyrazine (abbreviation: Hdppr-3FP)

To a reaction container for irradiation of a microwave were placed 0.20 g (1.0 mmol) of 1-(3-fluorophenyl)-2-(methylsulfinyl)ethanone, which is an intermediate and was obtained in the above Step 1, 0.21 g (1.0 mmol) of meso-1,2-diphenylethylenediamine, and 0.067 g (2.1 mmol) of sulfur (crystal), and 1 mL of ethanol was added to the mixture. This mixture was irradiated with a microwave (2.45 GHz, 50 to 100 W (change depending on reaction temperature and pressure)) for 60 minutes to be reacted. Note that the reaction temperature was set to be 70 to 75° C., and the reaction pressure was set to be 40 to 45 psi ($28 \times 10^4$ Pa to $31 \times 10^4$ Pa). After the reaction, to 100 mL of 1 M dilute hydrochloric acid was added the reaction mixture. Ethyl acetate was added to this reaction mixture to extract an organic layer, and the organic layer was separated. The separated organic layer was washed with 1 M dilute hydrochloric acid, a saturated aqueous sodium hydrogen carbonate solution, and a saturated aqueous sodium chloride solution in this order. After washing, magnesium sulfate was added to the organic layer to dry the organic layer. After drying, this mixture was subjected to suction filtration to remove magnesium sulfate, so that a filtrate was obtained. The obtained filtrate was concentrated, and was purified by silica gel column chromatography using dichloromethane as a developing solvent, so that a pyrazine derivative Hdppr-3FP (a brown oily substance, yield: 24%), which was a target substance was obtained. Note that the irradiation with a microwave was performed using a microwave synthesis system (Discover, produced by CEM Corporation). A synthetic scheme of Step 2 is shown by a following (b-1).

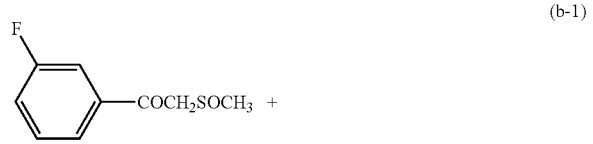

(b-1)

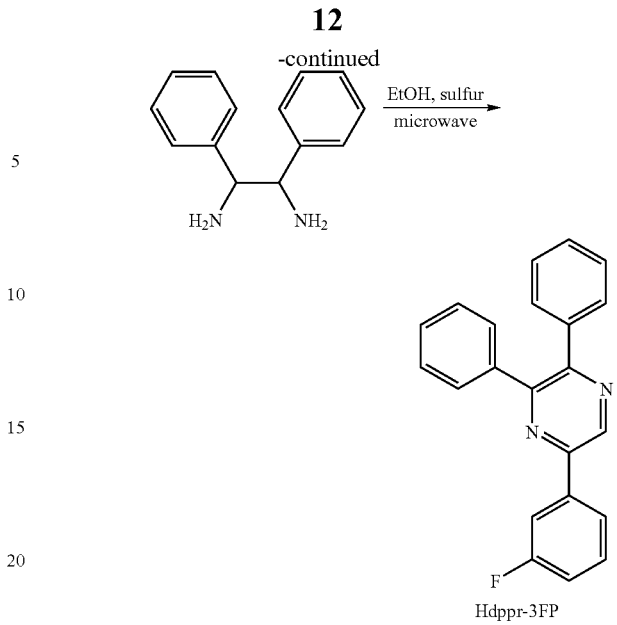

Figure 1B:
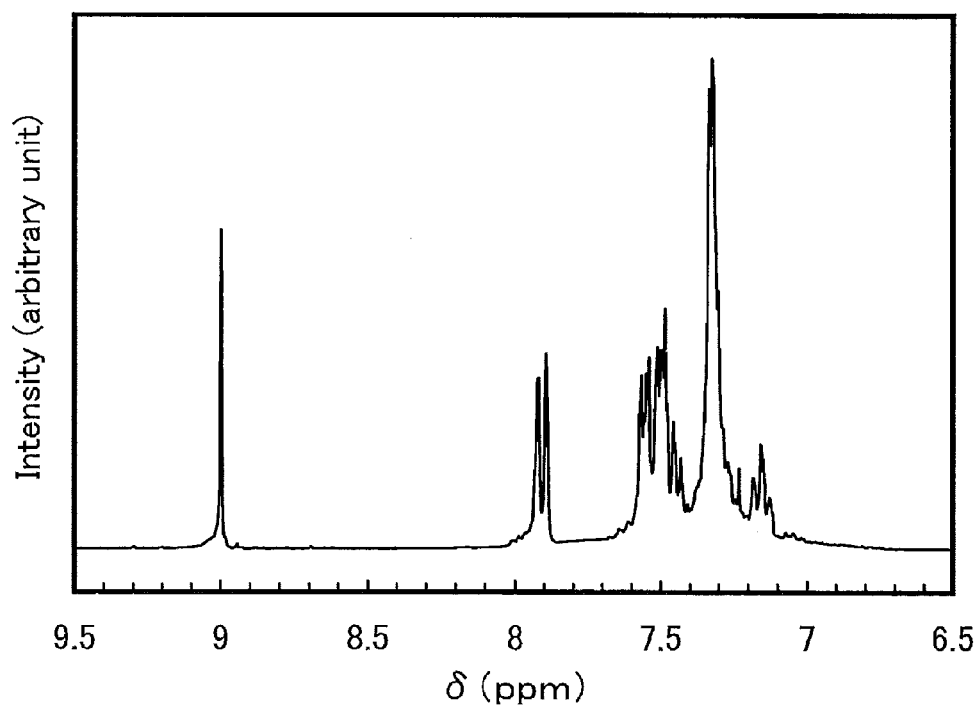

Note that a result of nuclear magnetic resonance spectrometry ($^1$H-NMR) in which the brown oily substance obtained in the above Step 2 was purified again, and was analyzed is shown below. In addition, $^1$H-NMR charts are shown in FIGS. 1A and 1B. From the result, it was found that Hdppr-3FP represented by the above structural formula (1) was obtained in this synthesis example.

$^1$H NMR (CDCl$_3$, 300 MHz): δ=7.11-7.60 (m, 12H), 7.91 (d, J=7.3 Hz, 2H), 8.99 (s, 1H).

In this synthetic example, the yield of Step 1 was 42%, and the yield of Step 2 was 24%. Thus, Hdppr-3FP could be obtained at a yield of about 10% in total.

Synthesis Example 2

In this synthesis example, another synthesis method of Hdppr-3FP, which is the arylpyrazine derivative shown as the structural formula (1) in Embodiment Mode 1 is described.

Step 1: Synthesis of Intermediate, 1-(3-fluorophenyl)-2-(methylsulfinyl)ethanone In the same manner as Step 1 in Synthesis Example 1, synthesis was performed.

Step 2: Synthesis of 5-(3-fluorophenyl)-2,3-diphenylpyrazine (abbreviation: Hdppr-3FP)

Next, to a three-necked flask were placed 2.5 g of 1-(3-fluorophenyl)-2-(methylsulfinyl)ethanone, which is an intermediate and was obtained in the above Step 1 and 2.7 g of meso-1,2-diphenylethylenediamine, and 65 mL of ethanol was added to the mixture. This mixed solution was stirred while being heated at 80° C. under a stream of nitrogen. This mixed solution was taken out to reaction containers in increments of 10 mL. After 0.1 g of iron(III) chloride was added to each reaction container, each mixture was irradiated with a microwave (2.45 GHz, 200 W) for 60 minutes to be reacted. After the reaction, these mixtures were concentrated, so that a solid was obtained. To the obtained solid was added dichloromethane, and this suspension was filtered through Celite (produced by Wako Pure Chemical Industries, Ltd., Catalog No. 531-16855) and alumina, so that a filtrate was obtained. The obtained filtrate was washed with 1 M dilute hydrochloric acid, a saturated aqueous sodium hydrogen carbonate solution, and a saturated aqueous sodium chloride solution in this order, and then dried with magnesium sulfate. This mixture was subjected to suction filtration to remove the magnesium sulfate, so that a filtrate was obtained. The obtained filtrate was concentrated, and was purified by silica gel column chromatography using dichloromethane as a developing solvent, so that a pyrazine derivative Hdppr-3FP (a brown oily substance, yield: 9.4%), which was a target substance was obtained. Note that the irradiation with a microwave was performed using a microwave synthesis system (Discover, produced by CEM Corporation). A synthetic scheme of Step 2 is shown by a following (b-2).

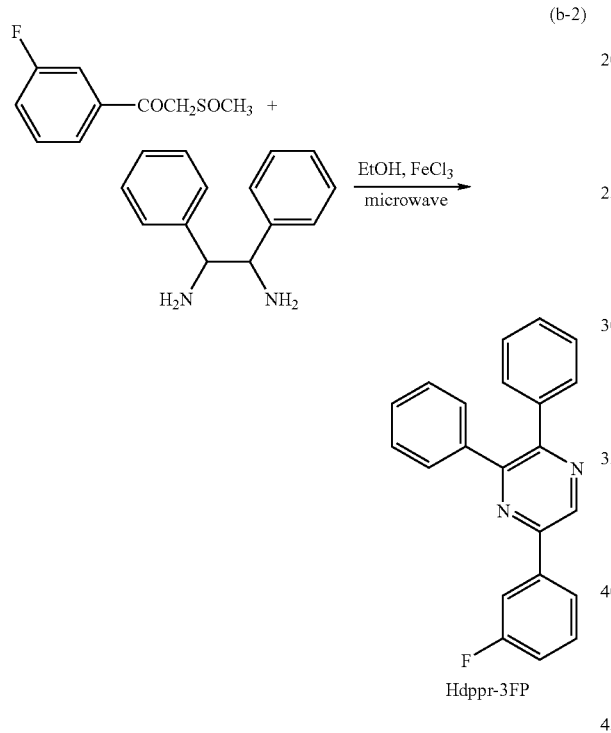

In this synthesis example, the yield of Step 1 was 42%, and the yield of Step 2 was 9.4%. Thus, Hdppr-3FP could be obtained at a yield of about 4% in total.

Synthesis Example 3

In this synthesis example, another synthesis method of Hdppr-3FP, which is the arylpyrazine derivative shown as the structural formula (1) in Embodiment Mode 1 is described.

Step 1: Synthesis of Intermediate, 1-(3-fluorophenyl)-2-(methylsulfinyl)ethanone In the same manner as Step 1 in Synthesis Example 1, synthesis was performed.

Step 2: Synthesis of 5-(3-fluorophenyl)-2,3-diphenylpyrazine (abbreviation: Hdppr-3FP)

To a reaction container for irradiation of a microwave were placed 0.20 g (1.0 mmol) of 1-(3-fluorophenyl)-2-(methylsulfinyl)ethanone, which is an intermediate and was obtained in the above Step 1, 0.21 g (1.0 mmol) of meso-1,2-diphenyl-ethylenediamine, and 0.067 g (2.1 mmol) of sulfur (crystal), and 1 mL of dimethylsulfoxide (abbreviation: DMSO) was added to the mixture. This mixture was irradiated with a microwave (2.45 GHz, 90 to 100 W (change depending on reaction temperature and pressure)) for 10 minutes to be reacted. Note that the reaction temperature was set to be 90 to 100° C., and the reaction pressure was set to be 50 to 55 psi ($34 \times 10^4$ Pa to $38 \times 10^4$ Pa). After the reaction, to 100 mL of 1 M dilute hydrochloric acid was added the reaction mixture. Ethyl acetate was added to this reaction mixture to extract an organic layer, and the organic layer was separated. The separated organic layer was washed with 1 M dilute hydrochloric acid, a saturated aqueous sodium hydrogen carbonate solution, and a saturated aqueous sodium chloride solution in this order. After washing, magnesium sulfate was added to the organic layer to dry the organic layer. After drying, this mixture was subjected to suction filtration to remove magnesium sulfate, so that a filtrate was obtained. The obtained filtrate was concentrated, and was purified by silica gel column chromatography using dichloromethane as a developing solvent, so that a pyrazine derivative Hdppr-3FP (a brown oily substance, yield: 21%), which was a target substance was obtained. Note that the irradiation with a microwave was performed using a microwave synthesis system (Discover, produced by CEM Corporation). A synthetic scheme of Step 2 is shown by a following (b-3).

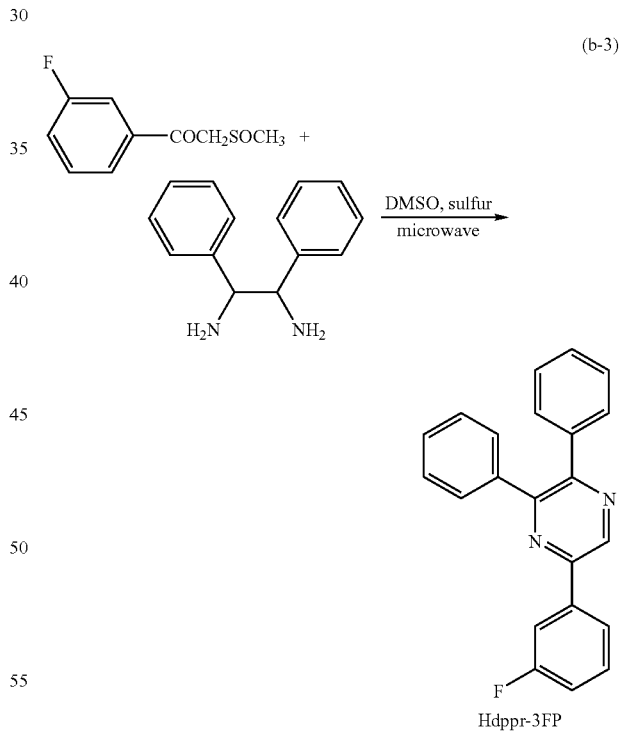

In this synthesis example, the yield of Step 1 was 42%, and the yield of Step 2 was 21%. Thus, Hdppr-3FP could be obtained at a yield of about 9% in total.

Synthesis Example 4

In this synthesis example, another synthesis method of Hdppr-3FP, which is the arylpyrazine derivative shown as the structural formula (1) in Embodiment Mode 1 is described.

Step 1: Synthesis of Intermediate, 1-(3-fluorophenyl)-2-methanesulfinylethanone In the same manner as Step 1 in Synthesis Example 1, synthesis was performed.

Step 2: Synthesis of 5-(3-fluorophenyl)-2,3-diphenylpyrazine (abbreviation: Hdppr-3FP)

To a reaction container for irradiation of a microwave were placed 0.21 g (1.0 mmol) of 1-(3-fluorophenyl)-2-methanesulfinylethanone, which is an intermediate and was obtained in the above Step 1, 0.20 g (1.0 mmol) of meso-1,2-diphenylethylenediamine, and 0.067 g (2.1 mmol) of sulfur (crystal), and 1 mL of 2-ethoxyethanol was added to the mixture. This mixture was irradiated with a microwave (2.45 GHz, 50 W) for 10 minutes to be reacted. Note that the reaction temperature was set to be 60° C., and the reaction pressure was set to be 10 to 15 psi ($6.9 \times 10^4$ Pa to $10 \times 10^4$ Pa). After the reaction, the reaction mixture was concentrated, and ethyl acetate was added to this reaction mixture. This mixture was washed with 1 M dilute hydrochloric acid, a saturated aqueous sodium hydrogen carbonate solution, and a saturated aqueous sodium chloride solution in this order. After washing, magnesium sulfate was added to the organic layer to dry the organic layer. After drying, this mixture was subjected to suction filtration to remove magnesium sulfate, so that a filtrate was obtained. The obtained filtrate was concentrated, and was purified by silica gel column chromatography using dichloromethane as a developing solvent, so that a pyrazine derivative Hdppr-3FP (a brown oily substance, yield: 21%), which was a target substance was obtained. Note that the irradiation with a microwave was performed using a microwave synthesis system (Discover, produced by CEM Corporation). A synthetic scheme of Step 2 is shown by a following (b-4).

In this synthesis example, the yield of Step 1 was 42%, and the yield of Step 2 was 21%. Thus, Hdppr-3FP could be obtained at a yield of about 9% in total.

Synthesis Example 5

In this synthesis example, another synthesis method of Hdppr-3FP, which is the arylpyrazine derivative shown as the structural formula (1) in Embodiment Mode 1 is described.

Step 1: Synthesis of Intermediate, 1-(3-fluorophenyl)-2-methanesulfinylethanone In the same manner as Step 1 in Synthesis Example 1, synthesis was performed.

Step 2: Synthesis of 5-(3-fluorophenyl)-2,3-diphenylpyrazine (abbreviation: Hdppr-3FP)

To a reaction container for irradiation of a microwave were placed 0.21 g (1.0 mmol) of 1-(3-fluorophenyl)-2-methanesulfinylethanone which is an intermediate and was obtained in the above Step 1, 0.20 g (1.0 mmol) of meso-1,2-diphenylethylenediamine, and 0.067 g (2.1 mmol) of sulfur (crystal), and 1 mL of acetonitrile was added to the mixture. This mixture was irradiated with a microwave (2.45 GHz, 0 to 100 W (change depending on reaction temperature and pressure)) for 10 minutes to be reacted. Note that the reaction temperature was set to be 75 to 85° C., and the reaction pressure was set to be 20 to 25 psi ($14 \times 10^4$ Pa to $17 \times 10^4$ Pa). After the reaction, the reaction mixture was concentrated, and ethyl acetate was added to this reaction mixture. This mixture was washed with 1 M dilute hydrochloric acid, a saturated aqueous sodium hydrogen carbonate solution, and a saturated aqueous sodium chloride solution in this order. After washing, magnesium sulfate was added to the organic layer to dry the organic layer. After drying, this mixture was subjected to suction filtration to remove magnesium sulfate, so that a filtrate was obtained. The obtained filtrate was concentrated, and was purified by silica gel column chromatography using dichloromethane as a developing solvent, so that a pyrazine derivative Hdppr-3FP (a brown oily substance, yield: 21%), which was a target substance was obtained. Note that the irradiation with a microwave was performed using a microwave synthesis system (Discover, produced by CEM Corporation). A synthetic scheme of Step 2 is shown by a following (b-5).

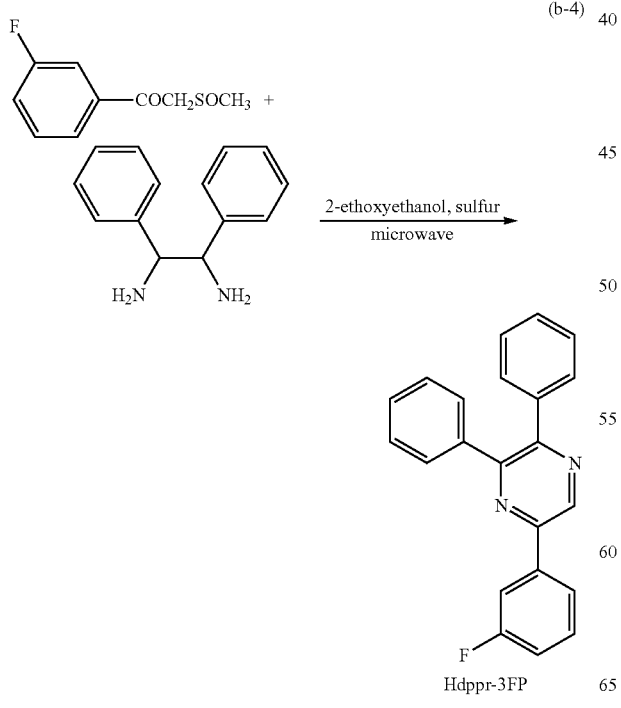

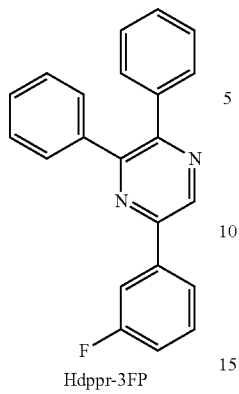

Hdppr-3FP

In this synthesis example, the yield of Step 1 was 42%, and the yield of Step 2 was 21%. Thus, Hdppr-3FP could be obtained at a yield of about 9% in total.

Comparative Synthesis Example 1

As a comparative example, a synthesis method of Hdppr-3FP in which 2,3-diphenylamine obtained by dehydration condensation of α-diketone and diamine, and an oxidative dehydrogenation reaction following the dehydration condensation is reacted with an aryllithium compound is described.

Step 1: Synthesis of Ligand Hdppr

First, 21.0 g (100 mmol) of benzyl and 6.1 g (101 mmol) of ethylenediamine are refluxed using 300 mL of dehydrated ethanol as a solvent for 6 hours under an atmosphere of nitrogen. Further, the solution was concentrated to one fifth, and a precipitated sediment was collected. The obtained sediment was washed with cool ethanol, so that 2,3-diphenyl-5,6-dihydropyridine was obtained (yield: 78%).

Next, 18.3 g (78.2 mmol) of 2,3-diphenyl-5,6-dihydropyrazine and 4.4 g of potassium hydroxide were added to 200 mL of dissolved glycerin, and stirred while being heated at 190° C. for 20 minutes. After cooling, an organic layer was extracted with ether a plurality of times, and ether was removed, and then the mixture was purified with column using a solvent of ethyl acetate/hexane. By removing the solvent of ethyl acetate/hexane, a ligand Hdppr(2,3-diphenylpyrazine) (an apricot orange powder, yield: 22%) was obtained. A reaction in this step is shown as a formula (c-1).

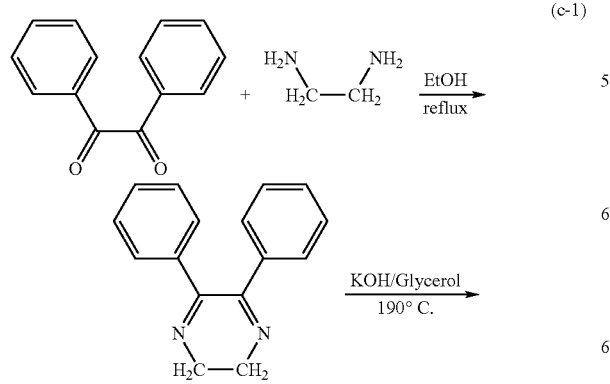

(c-1)

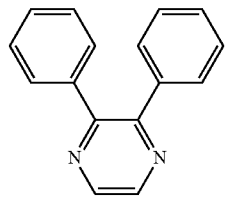

Step 2: Synthesis of 5-(3-fluorophenyl)-2,3-diphenylpyrazine (abbreviation: Hdppr-3FP)

First, 7.5 mL (1.58 mol/L) of hexane solution of n-butyllithium was added dropwise to a mixed solution of 1.49 g of 3-bromofluorobenzene and 11 mL of tetrahydrofuran at −78° C. under an atmosphere of nitrogen, and stirred for 30 minutes, keeping the temperature at −78° C. The obtained solution was added dropwise to a mixed solution, which was cooled with ice, of 2.45 g of 2,3-diphenylpyrazine and 20 mL of tetrahydrofuran, and stirred for 1 hour at room temperature. Water was added to this mixture and an organic layer was extracted using ethyl acetate as an extraction solvent. The obtained organic layer was washed with water and dried with anhydrous magnesium sulfate. After drying, the solution was filtrated. The solvent of the solution was distilled off and the residue obtained by distillation was purified by silica gel column chromatography using dichloromethane as a developing solvent. In this way, Hdppr-3FP (an orange powder, yield: 8%), which was a target substance was obtained. A synthetic scheme of Step 1 is shown by a following (c-2).

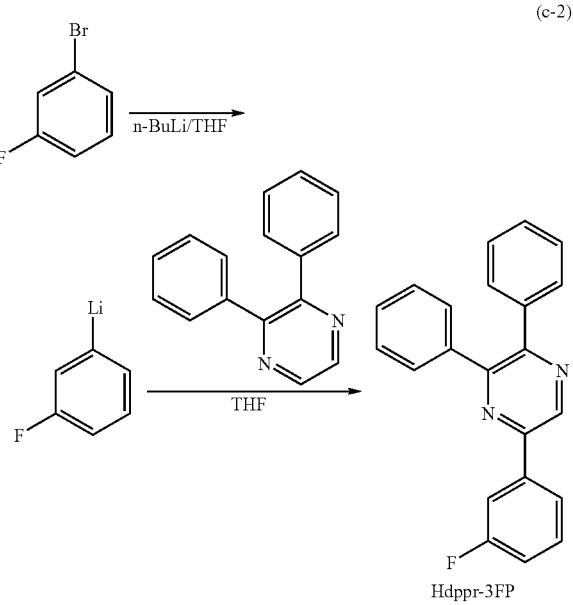

(c-2)

In this comparative synthesis example 1, the yield of Step 1 was 78%×22%, i.e., about 17%, and the yield of Step 2 was 8%. Thus, the yield in total is about 1%. The yield of Synthesis Examples 1 to 5 in Embodiments of the present invention in total is 4 to 10%; thus, by using a synthesis method of the present invention, Hdppr-3FP can be obtained at a yield of 4 to 10 times as high as that of the comparative synthesis example 1. Note that, when Hdppr-3FP obtained by Synthesis Example 1 was purified again, the obtained Hdppr-3FP was about half of the Hdppr-3FP before being purified again. This is probably because adsorption of Hdppr-3FP to column is large; however, even though the yield is half of the Hdppr-3FP before being purified again, the yield is 2 to 5 times as large as a yield of the comparative synthesis example 1, so a method according to the present invention is still superior.

Embodiment 2

Synthesis Example 6

In this synthesis example, a synthesis method of 5-(3,5-difluorophenyl)-2,3-diphenylpyrazine (abbreviation: Hdppr-3,5FP) represented by the following structural formula (2) is described.

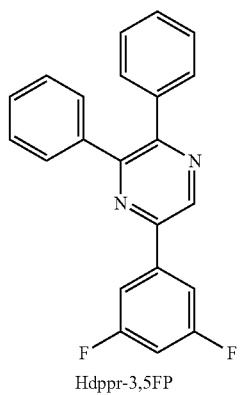

Hdppr-3,5FP (2)

Step 1; Synthesis of Intermediate, 3,5-difluoromethyl benzoate

First, to a round-bottomed flask equipped with a reflux pipe were placed 10.57 g of 3,5-difluoro benzoate, 40 mL of methanol, and 2 mL of sulfuric acid, and the atmosphere in the flask was replaced with argon. Then, it was irradiated with a microwave (2.45 GHz, 100 W) for 10 minutes to be reacted. After the reaction, methanol was distilled off from the reaction solution, and 50 mL of water was added to a residue. This aqueous solution was neutralized with 20% aqueous sodium hydroxide solution to extract an organic layer by adding hexane. After extracting, magnesium sulfate was added to the obtained organic layer to dry the organic layer. After drying, magnesium sulfate was removed by natural filtration. Hexane was distilled off from the obtained filtrate, so that an intermediate, 3,5-difluoromethyl benzoate (a white powder, yield: 42%) which was precipitated, was obtained. A synthetic scheme of Step 1 is shown by a following (a'-6).

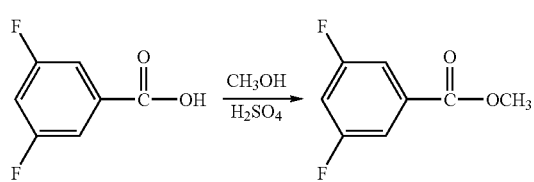

(a'-6)

Step 2; Synthesis of Intermediate, 1-(3,5-difluorophenyl)-2-(methylsulfinyl)ethanone Next, to a three-necked flask was placed 2.28 g of 60% sodium hydride (oily), and was added petroleum ether, and then the flask was shaken to mix its contents. After that, petroleum ether was discarded by decantation. After this washing operation of sodium hydride with petroleum ether was repeated three times, sodium hydride was dried under reduced pressure. After drying, to sodium hydride was added dropwise 40 mL of dimethylsulfoxide. The mixture was stirred while being heated at 70° C. for 1 hour to be reacted. After the reaction, the reaction mixture was cooled down to room temperature. The mixture was cooled with ice, and 40 mL of tetrahydrofuran (THF) was added to the mixture. After that, 4.89 g of 3,5-difluoroethyl benzoate obtained in the above Step 1 was added dropwise for 5 minutes. This mixture was stirred at room temperature for 30 minutes to be reacted. After the reaction, this mixture was poured into 80 mL of water in a plurality of steps, and this aqueous solution was adjusted so that pH thereof is 3 with 1 M dilute hydrochloric acid. To this solution was added chloroform, and an organic layer was extracted. After extracting, the organic layer was washed with water three times. After washing, sodium sulfate was added to the organic layer to dry the organic layer. After drying, sodium sulfate was removed by natural filtration. Chloroform was distilled off from the obtained filtrate, and the obtained mixture was recrystallized by isopropylether, so that an intermediate, 1-(3,5-difluorophenyl)-2-(methylsulfinyl)ethanone (a white solid, yield: 16%), was obtained. A synthetic scheme of Step 2 is shown by a following (a-6).

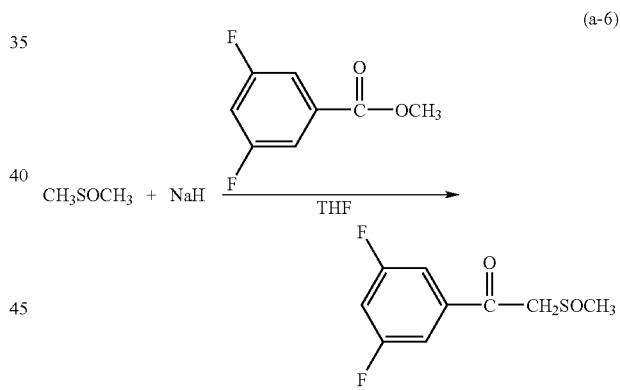

(a-6)

Step 3: Synthesis of 5-(3,5-difluorophenyl)-2,3-diphenylpyrazine (abbreviation: Hdppr-3,5FP)

Next, 0.55 g of 1-(3,5-fluorophenyl)-2-(methylsulfinyl)ethanone which is an intermediate and was obtained in the above Step 2, 0.54 g of meso-1,2-diphenylethylenediamine, 5 mL of dimethylsulfoxide, and 0.17 g of sulfur were mixed, and this mixture was irradiated with a microwave (2.45 GHz, 50 to 120 W (change depending on reaction temperature and pressure)) for 10 minutes to be reacted. Note that the reaction temperature was set to be 110 to 115° C., and the reaction pressure was set to be 30 to 45 psi ($21 \times 10^4$ Pa to $31 \times 10^4$ Pa). After the reaction, 1 M hydrochloric acid was added to the reaction solution, and an organic layer was extracted with ethyl acetate. Magnesium sulfate was added to this organic layer to dry the organic layer. After drying, magnesium sulfate was removed by natural filtration. Ethyl acetate was distilled off from the obtained filtrate, and the obtained residue was purified by silica gel column chromatography using dichloromethane as a developing solvent, so that a pyrazine derivative Hdppr-3,5FP (a brown oily substance, yield: 15%), which was a target substance was obtained. A synthetic scheme of Step 3 is shown by a following (b-6).

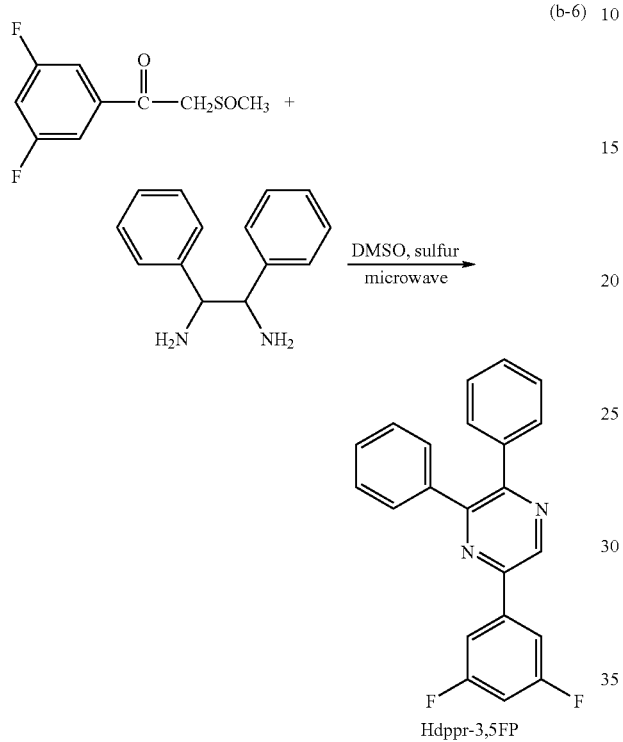

In this synthesis example, the yield of Step 1 was 42%, the yield of Step 2 was 16%, and the yield of Step 3 was 15%. Thus, Hdppr-3,5FP could be obtained at a yield of about 1% in total. Note that, in the Step 2 in this synthesis example, there was a point to be improved in terms of reaction operation. If this point is improved, a yield which is equal or near to the yield of the Synthesis Example 1 in Embodiment 1 can be obtained, so that it is inferred that the real yield of this synthesis example is a little higher.

Figure 2A:
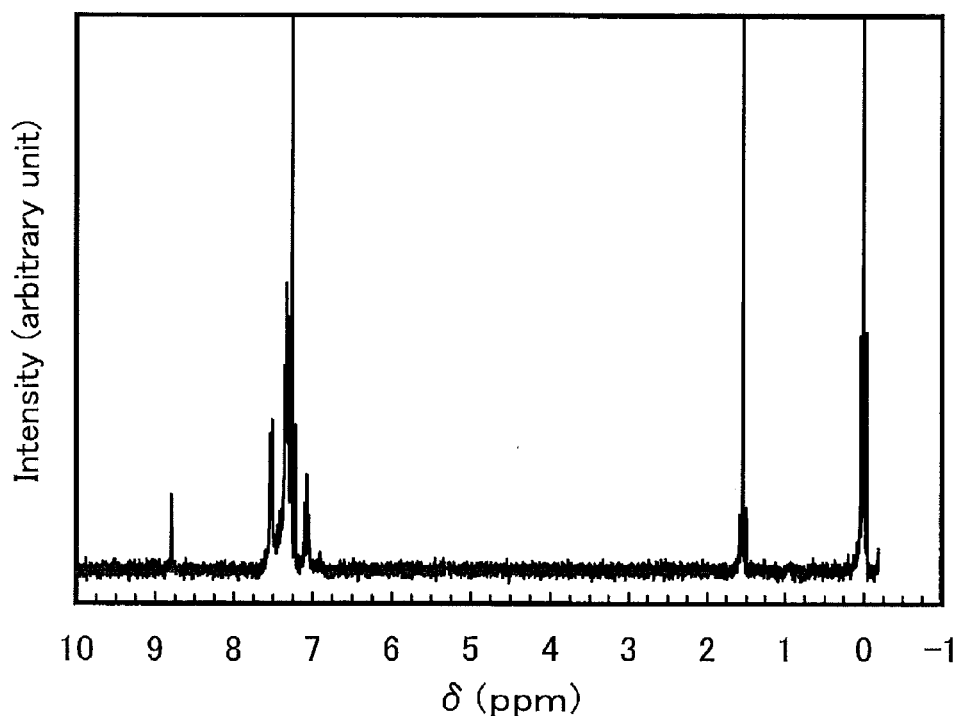
FIGS. 2A and 2B are NMR charts of 5-(3,5-difluorophenyl)-2,3-diphenylpyrazine which was synthesized in Synthesis Example 6 in Embodiment 2.
Figure 2B:
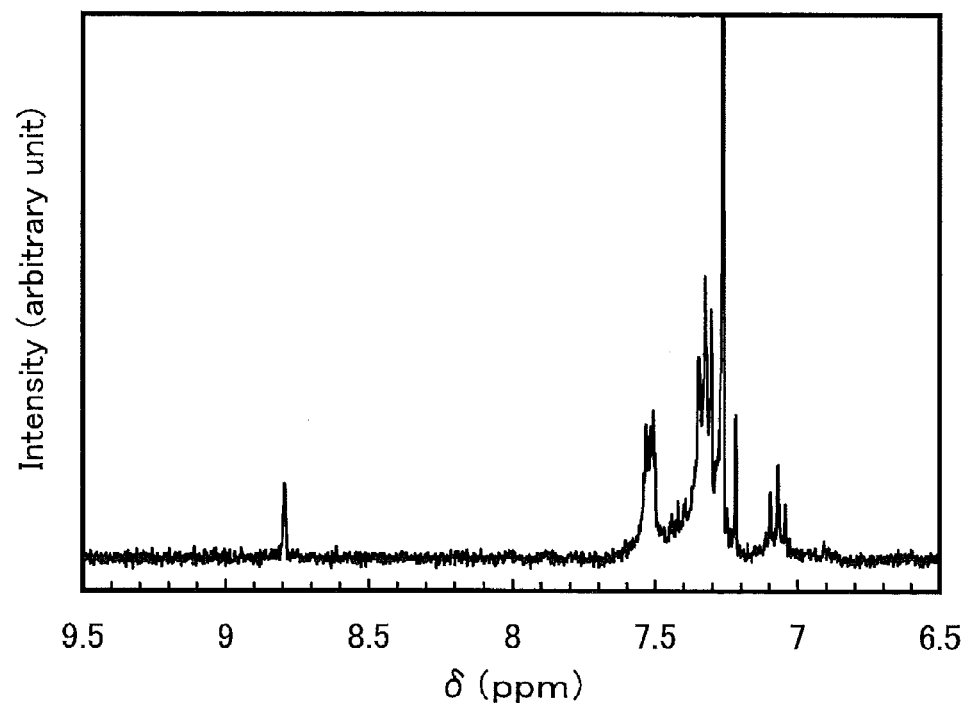

Note that a result of nuclear magnetic resonance spectrometry ($^1$H-NMR) in which the brown oily substance obtained in the above Step 3 was analyzed is shown below. In addition, $^1$H-NMR charts are shown in FIGS. 2A and 2B. From the result, it was found that the Hdppr-3,5FP represented by the above structural formula (2) was obtained in this synthesis example.

$^1$H-NMR. δ (CDCl$_3$): 7.07 (t, 2H), 7.33 (m, 7H), 7.51 (m, 4H), 8.80 (s, 1H).

Note that, as far as seen in FIGS. 2A and 2B, the amount of mixture of an impurity is not so large; thus, Hdppr-3,5FP was not purified again.

Comparative Synthesis Example 2

As a comparative example, a conventional synthesis method of Hdppr-3,5FP in which 2,3-diphenylamine obtained by dehydration condensation of α-diketone and diamine and oxidative dehydrogenation reaction following the dehydration condensation is reacted with an aryl lithium compound is described.

Step 1: Synthesis of Ligand Hdppr

In the same manner as Step 1 in Comparative Synthesis Example 1 in Embodiment 1, synthesis was performed (yield in total: about 17%).

Step 2: Synthesis of 5-(3,5-difluorophenyl)-2,3-diphenylpyrazine (abbreviation: Hdppr-3,5FP)

First, to a mixed solution of 4.02 g of 1-bromo-3,5-difluorobenzene and 40 mL of tetrahydrofuran was added dropwise 14 mL (1.61 mol/L) of hexane solution of n-butyllithium at −78° C. under an atmosphere of nitrogen, and the solution was stirred for 2 hours at −78° C. In addition, to this mixed solution was added 4.03 g of 2,3-diphenylpyrazine in five steps at −78° C., and the temperature of the solution was raised to room temperature. Water was added to this mixture and an organic layer was extracted using diethylether as an extraction solvent. The obtained organic layer was washed with water and dried with anhydrous magnesium sulfate. The solution after drying was filtrated, and the magnesium sulfate was removed. The solvent of the solution was distilled off and the residue obtained by distillation was purified by silica gel column chromatography using dichloromethane as a developing solvent, so that a pyrazine derivative Hdppr-3,5FP (an orange powder, yield: 4%), which was a target substance was obtained. A synthetic scheme of Step 2 is shown by a following (c-3).

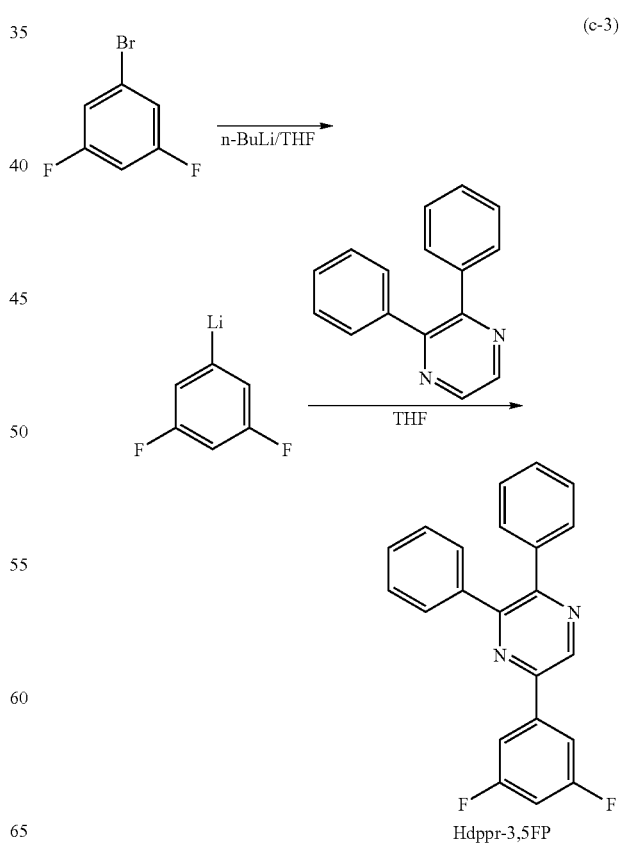

In Comparative Synthesis Example 2, the yield of Step 1 was about 17%, and the yield of Step 2 was 4%. Thus, the yield in total is about 0.7%. Since the yield of Synthesis Example 4 which is an Embodiment of the present invention is 1% in total, Hdppr-3,5FP can be obtained at a yield raised by 40% as compared to the comparative synthesis example 2 by using a synthesis method of the present invention.

Embodiment 3

In this embodiment, by using Hdppr-3FP which was synthesized, a synthesis method of (acetylacetonato)bis[5-(3-fluorophenyl)-2,3-diphenylpyrazinato]iridium(III) (abbreviation: [Ir(dppr-3FP)$_2$(acac)]), which is an organometallic complex represented by a following structural formula (3), characteristics of the complex, and a light-emitting element using the complex are described.

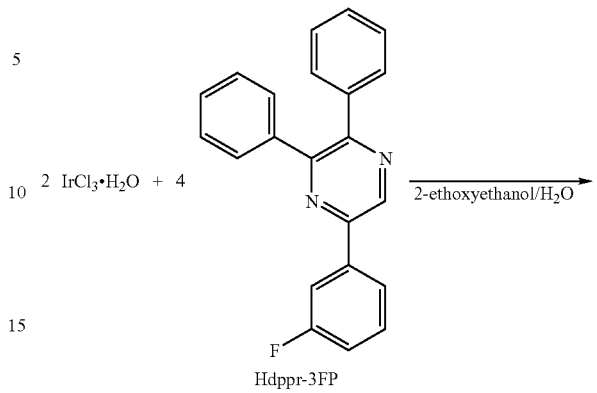

(d-1)

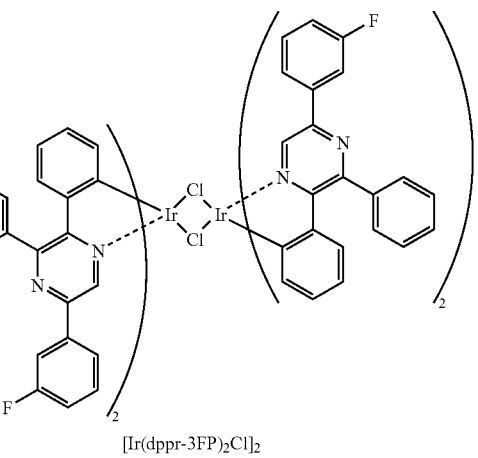

(3)

[Ir(dppr-3FP)$_2$(acac)]

Synthesis Example 7

Step 1: Synthesis of di-μ-chloro-bis[bis{5-(3-fluorophenyl)-2,3-diphenylpyrazinato}iridium(III)] (abbreviation: [Ir(dppr-3FP)$_2$Cl]$_2$)

To a recovery flask equipped with a reflux pipe were placed 4.5 mL of 2-ethoxyethanol, 1.5 mL of water, 0.40 g of a pyrazine derivative Hdppr-3FP, and 0.18 g of iridium chloride hydrate (IrCl$_3$.H$_2$O) (produced by Sigma-Aldrich Corporation), and the atmosphere in the flask was replaced with argon. Then, it was irradiated with a microwave (2.45 GHz, 200 W) for 5 hours to be reacted. The orange powder which was precipitated from the reaction solution was filtered, and washed with ethanol, so that a binuclear complex [Ir(dppr-3FP)$_2$Cl]$_2$ was obtained (yield: 12%). Note that the irradiation with a microwave was performed using a microwave synthesis system (Discover, produced by CEM Corporation). A synthetic scheme of Step 1 is shown by a following (d-1).

Step 2: Synthesis of (acetylacetonato)bis[5-(3-fluorophenyl)-2,3-diphenylpyrazinato]iridium(III) (Abbreviation: [Ir(dppr-3FP)$_2$(acac)]

Following the Step 1, to a recovery flask equipped with a reflux pipe were placed 5 mL of 2-ethoxyethanol, 0.13 g of the binuclear complex [Ir(dppr-3FP)$_2$Cl]$_2$ which was obtained in the above Step 1, 0.02 mL of acetylacetone, and 0.078 g of sodium carbonate, and the atmosphere in the flask was replaced with argon. Then, it was irradiated with a microwave (2.45 GHz, 100 W) for 15 minutes to be reacted. The reaction solution was filtered, and the solvent of the obtained filtrate was distilled off. A residue obtained by distillation was recrystallized with methanol, so that an organometallic complex of the present invention, [Ir(dppr-3FP)$_2$(acac)] (a red powder, yield: 100%) was obtained. A synthetic scheme of Step 2 is shown by a following (d-2).

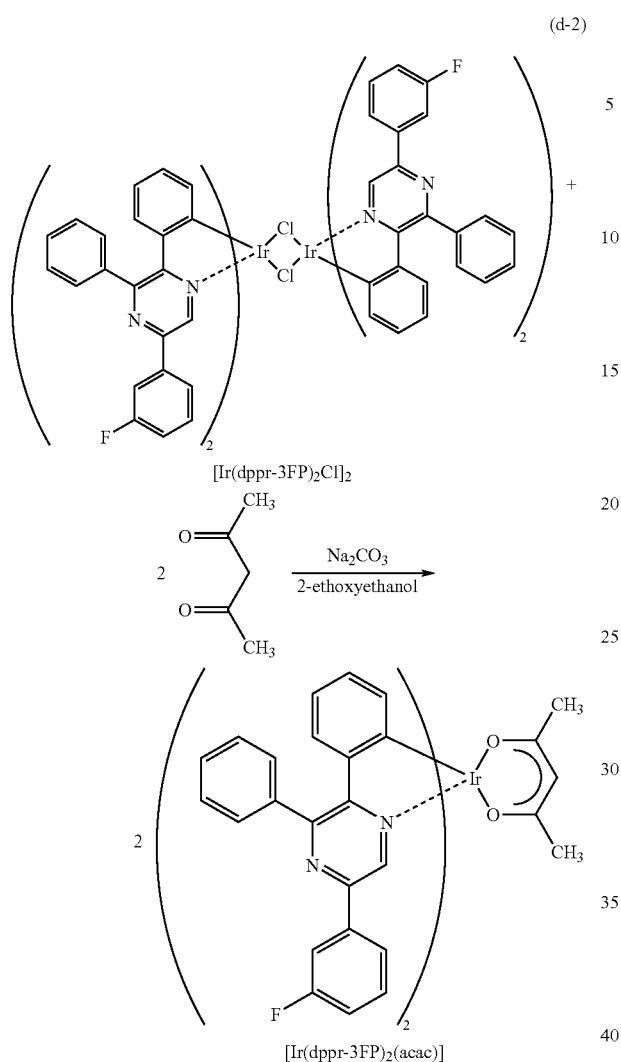

[Ir(dppr-3FP)₂Cl]₂

[Ir(dppr-3FP)₂(acac)]

Note that a result of nuclear magnetic resonance spectrometry (¹H-NMR) in which the brown oily substance obtained in the above Step 2 was analyzed is shown below. From the result, it was found that the organometallic complex [Ir(dppr-3FP)$_2$(acac)] represented by the above structural formula (3) was obtained in this synthesis example.

¹H-NMR. δ (CDCl$_3$): 1.94 (s, 6H), 5.37 (s, 1H), 6.45 (d, 2H), 6.52 (t, 2H), 6.68 (t, 2H), 6.93 (d, 2H), 7.16 (m, 2H), 7.48 (m, 2H), 7.53-7.61 (m, 6H), 7.79-7.86 (m, 8H), 8.94 (s, 2H).

Figure 3:
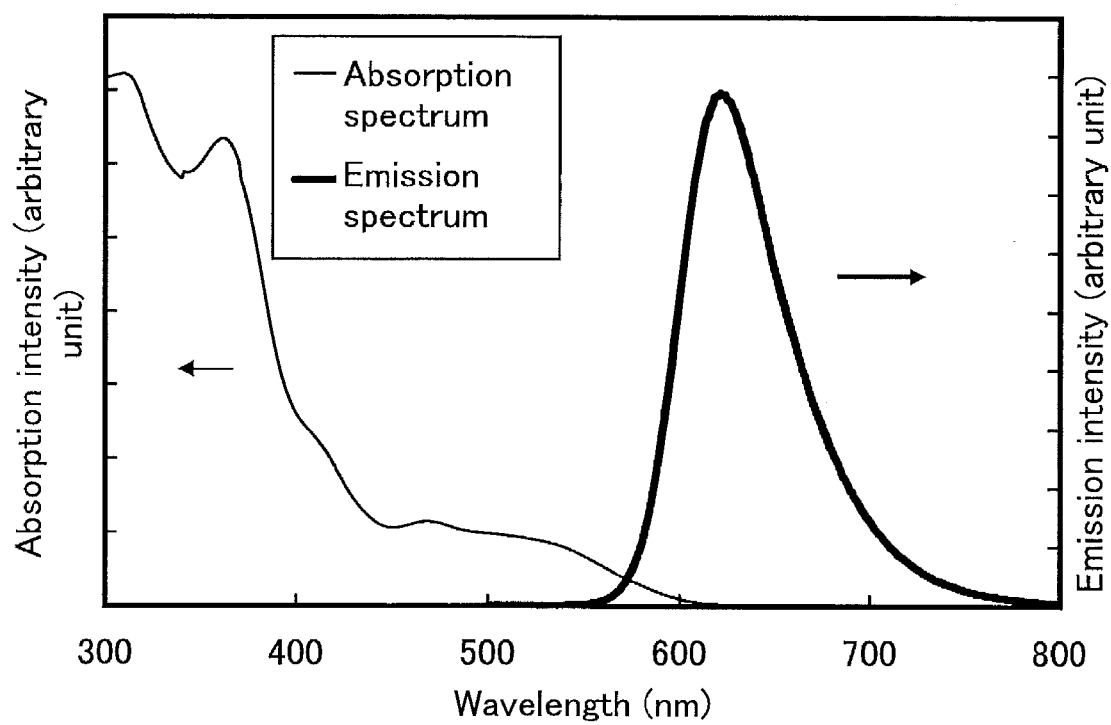
FIG. 3 is a graph showing an absorption spectrum and an emission spectrum of (acetylacetonato)bis[5-(3-fluorophenyl)-2,3-diphenylpyrazinato]iridium(III).

Next, an absorption spectrum of [Ir(dppr-3FP)$_2$(acac)] was measured. With the use of an ultraviolet-visible light spectrophotometer (manufactured by Japan Spectroscopy Corporation, V550 type), the absorption spectrum was measured using a chloroform solution at room temperature. Further, an emission spectrum of [Ir(dppr-3FP)$_2$(acac)] was measured. With the use of a fluorescence spectrophotometer (manufactured by Hamamatsu Photonics Corporation, FS920), the emission spectrum was measured using a degassed chloroform solution at room temperature. Measurement results are shown in FIG. 3. In FIG. 3, the horizontal axis represents wavelength and the vertical axis represents absorption intensity and emission intensity.

As shown in FIG. 3, [Ir(dppr-3FP)$_2$(acac)] has a peak of emission spectrum at 622 nm, and red light was observed from the chloroform solution.

Figure 4:
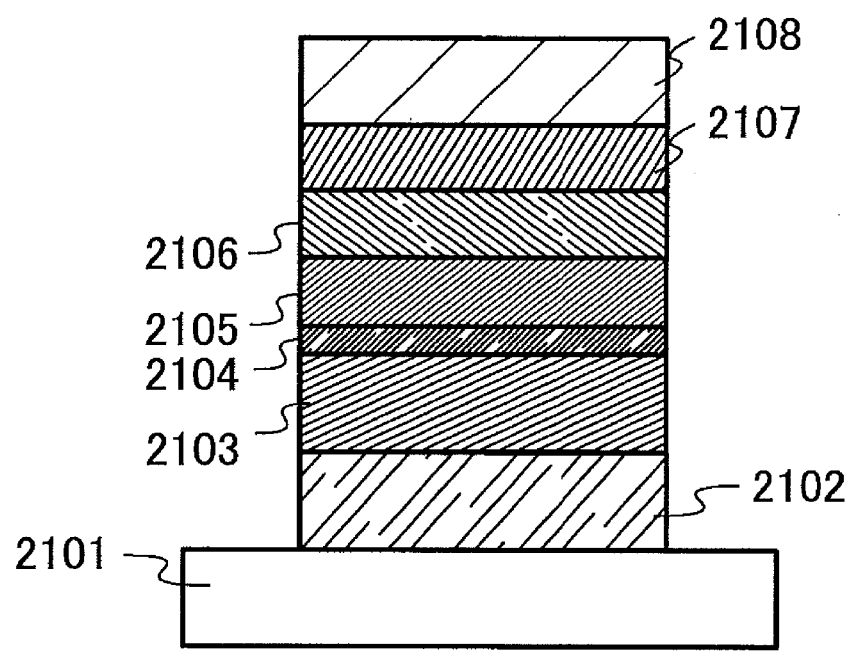
FIG. 4 is a diagram illustrating a light-emitting element of the present invention.

Then, a light-emitting element is described with reference to FIG. 4. A chemical formula of a material used for the light-emitting element is described below.

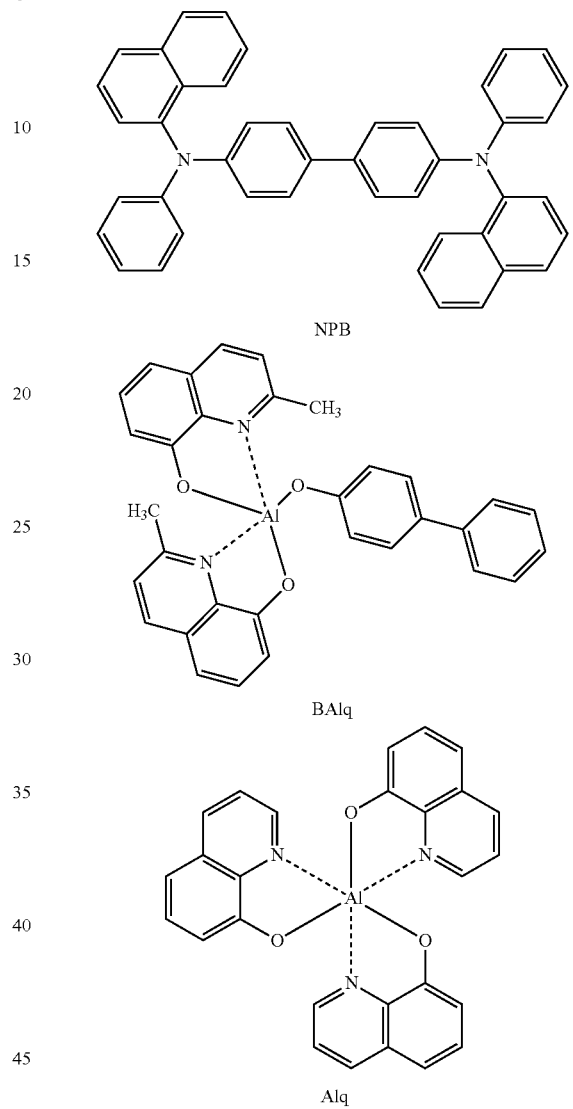

NPB

BAlq

Alq

First, a film of indium tin oxide containing silicon oxide was formed over a glass substrate 2101 by a sputtering method to form a first electrode 2102. Note that the thickness was 110 nm and the electrode area was 2 mm×2 mm.

Next, the substrate provided with the first electrode was fixed to a substrate holder provided in a vacuum evaporation apparatus so that the side on which the first electrode was formed faced downward. After the pressure was lowered to approximately $10^{-4}$ Pa, a layer 2103 containing a composite material of an organic compound and an inorganic compound was formed on the first electrode 2102 by co-evaporation of NPB and molybdenum(VI) oxide. The thickness was 50 nm and the weight ratio of NPB to molybdenum(VI) oxide was adjusted to be 4:1 (=NPB:molybdenum oxide). Note that a co-evaporation method refers to an evaporation method by which evaporation is concurrently conducted from a plurality of evaporation sources in one treatment chamber.

Next, a film of 4,4'-bis[N-(1-naphthyl)-N-phenylamino] biphenyl (Abbreviation: NPB) was formed to have a thickness of 10 nm on the layer 2103 containing a composite material by an evaporation method employing resistance heating, so that a hole-transporting layer 2104 was formed.

In addition, bis(2-methyl-8-quinolinolato)(4-phenylphenolato)aluminum (abbreviation: BAlq) and (acetylacetonato) bis[5-(3-fluorophenyl)-2,3-diphenylpyrazinato]iridium(III) (abbreviation: [Ir(dppr-3FP)$_2$(acac)]) represented by the structural formula (1) were co-evaporated, so that a light-emitting layer 2105 having a thickness of 50 nm was formed on the hole-transporting layer 2104. Here, the weight ratio of BAlq to Ir(dppr-3FP)$_2$(acac) was adjusted to be 1:0.05 (=BAlq: Ir(dppr-3FP)$_2$(acac)).

Then, a film of tris(8-quinolinolato)aluminum (abbreviation: Alq) was formed to have a thickness of 30 nm on the light-emitting layer 2105 by an evaporation method employing resistance heating, so that an electron-transporting layer 2106 was formed.

Further, an electron-injecting layer 2107 was formed on the electron-transporting layer 2106 by evaporating lithium to have a thickness of 1 nm.

Lastly, a film of aluminum was formed to have a thickness of 200 nm on the electron-injecting layer 2107 by an evaporation method employing resistance heating to form a second electrode 2108. Accordingly, a light-emitting element 1 was manufactured.

Figure 5:
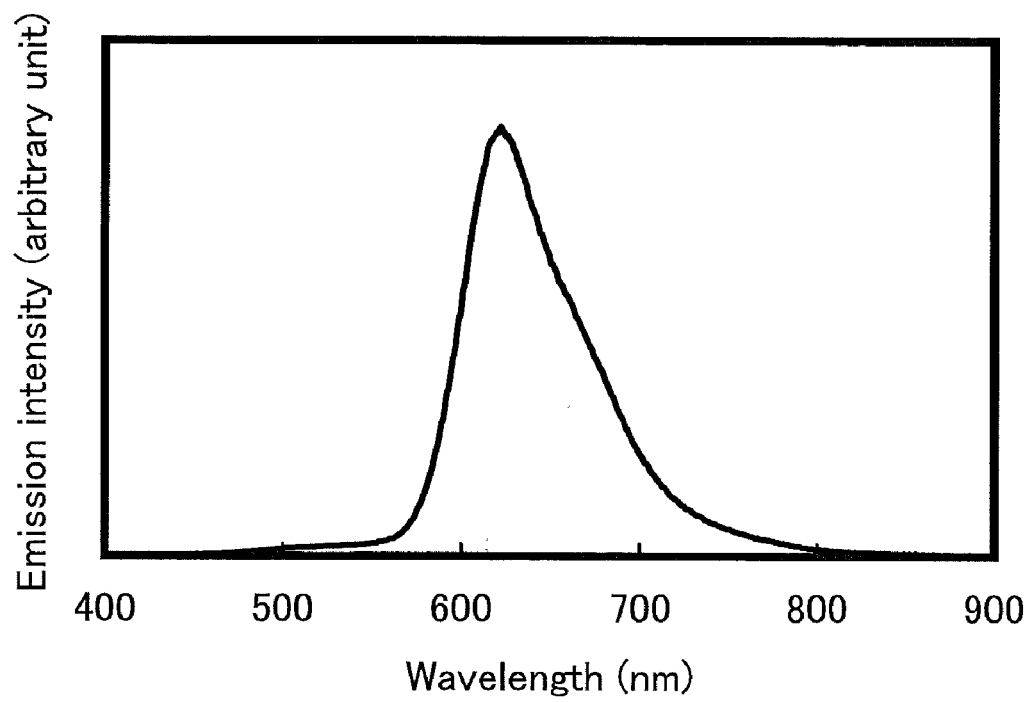
FIG. 5 is a graph showing an emission spectrum of a light-emitting element 1.

FIG. 5 shows an emission spectrum when a current of 1 mA flows to the light-emitting element 1. As shown in FIG. 5, it is found that the light-emitting element including Ir(dppr-3FP)$_2$(acac), which is an organometallic complex synthesized by using Hdppr-3FP and the synthesis of which is facilitated by a synthesis method of the present invention in a light-emitting layer, has a peak of the light emission at 622 nm and exhibits a favorable red light emission.

Embodiment 4

Synthesis Example 8

In this embodiment, by using Hdppr-3,5FP, a synthesis method of (acetylacetonato)bis[5-(3,5-difluorophenyl)-2,3-diphenylpyrazinato]iridium(III) (abbreviation: [Ir(dppr-3,5FP)$_2$(acac)]) represented by a following structural formula (4) and characteristics of the complex are described.

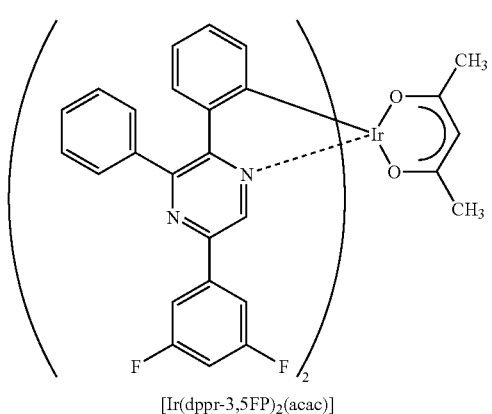

[Ir(dppr-3,5FP)$_2$(acac)] (4)

Step 1: Synthesis of di-μ-chloro-bis[bis {5-(3,5-difluorophenyl)-2,3-diphenylpyrazinato}iridium(III)] (abbreviation: [Ir(dppr-3,5FP)$_2$Cl]$_2$)

To a recovery flask equipped with a reflux pipe were placed 3 mL of 2-ethoxyethanol, 1 mL of water, 0.23 g of a pyrazine derivative Hdppr-3,5FP, and 0.08 g of iridium chloride hydrate (IrCl$_3$.H$_2$O) (produced by Sigma-Aldrich Corporation), and the atmosphere in the flask was replaced with argon. Then, it was irradiated with a microwave (2.45 GHz, 100 W) for 30 minutes to be reacted. The orange powder which was precipitated from the reaction solution was filtered and washed with ethanol, so that a binuclear complex [Ir(dppr-3,5FP)$_2$Cl]$_2$ was obtained (yield: 43%). Note that the irradiation with a microwave was performed using a microwave synthesis system (Discover, produced by CEM Corporation). A synthetic scheme of Step 1 is shown by a following (e-1).

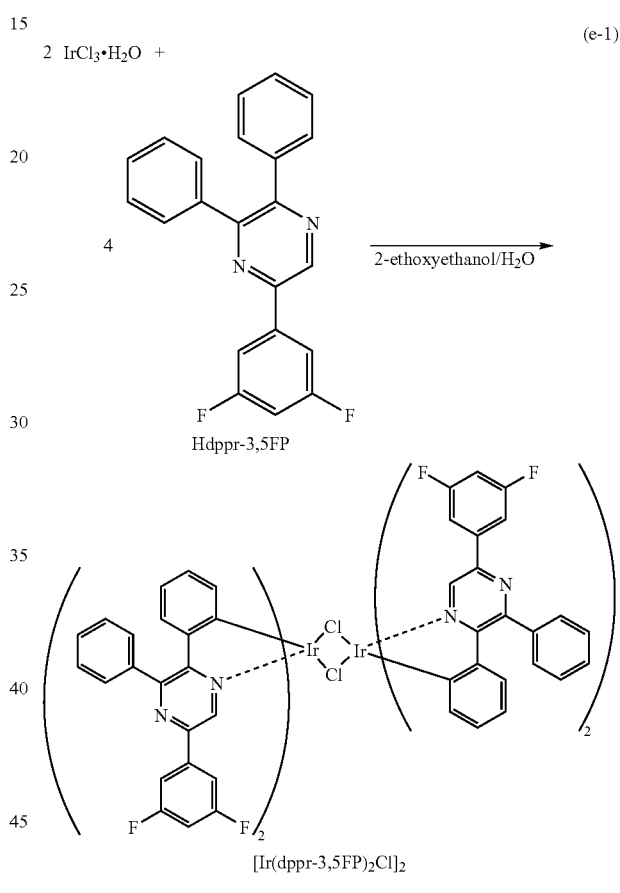

Step 2: Synthesis of (acetylacetonato)bis[5-(3,5-difluorophenyl)-2,3-diphenylpyrazinato]iridium(III) (abbreviation: [Ir(dppr-3,5FP)$_2$(acac)])

Following the Step 1, to a recovery flask equipped with a reflux pipe were placed 4 mL of 2-ethoxyethanol, 0.11 g of the binuclear complex [Ir(dppr-3,5FP)$_2$Cl]$_2$ obtained in the above Step 1, 0.02 mL of acetylacetone, and 0.064 g of sodium carbonate, and the atmosphere in the flask was replaced with argon. Then, it was irradiated with a microwave (2.45 GHz, 100 W) for 30 minutes to be reacted. The reaction solution was filtered, and the solvent of the obtained filtrate was distilled off. A residue obtained by distillation was recrystallized with methanol, so that an organometallic complex of the present invention, [Ir(dppr-3,5FP)$_2$(acac)] (a red powder, yield: 17%) was obtained. A synthetic scheme of Step 2 is shown by a following (e-2).

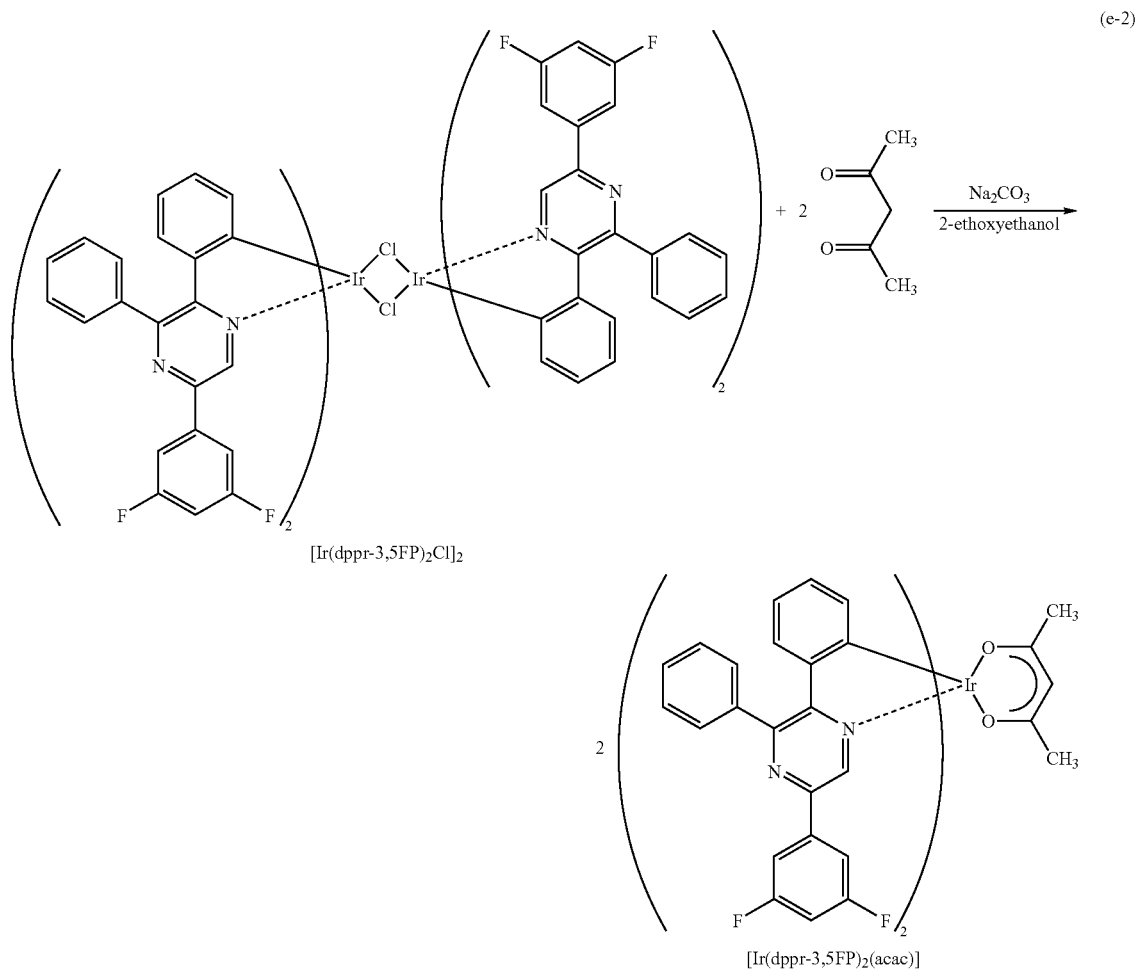

[Ir(dppr-3,5FP)₂Cl]₂

[Ir(dppr-3,5FP)₂(acac)]

Note that a result of nuclear magnetic resonance spectrometry ($^1$H-NMR) in which the brown oily substance obtained in the above Step 2 was analyzed is shown below. From the result, it was found that the organometallic complex [Ir(dppr-3,5FP)₂(acac)] was obtained in this Synthesis Example 8.

$^1$H-NMR. δ (CDCl₃): 1.89 (s, 6H), 5.32 (s, 1H), 6.52 (m, 3H), 6.71 (t, 1H), 6.95 (d, 2H), 7.05 (t, 3H), 7.40 (m, 2H), 7.53 (brm, 9H), 7.79 (brm, 4H), 8.76 (s, 2H).

Figure 6:
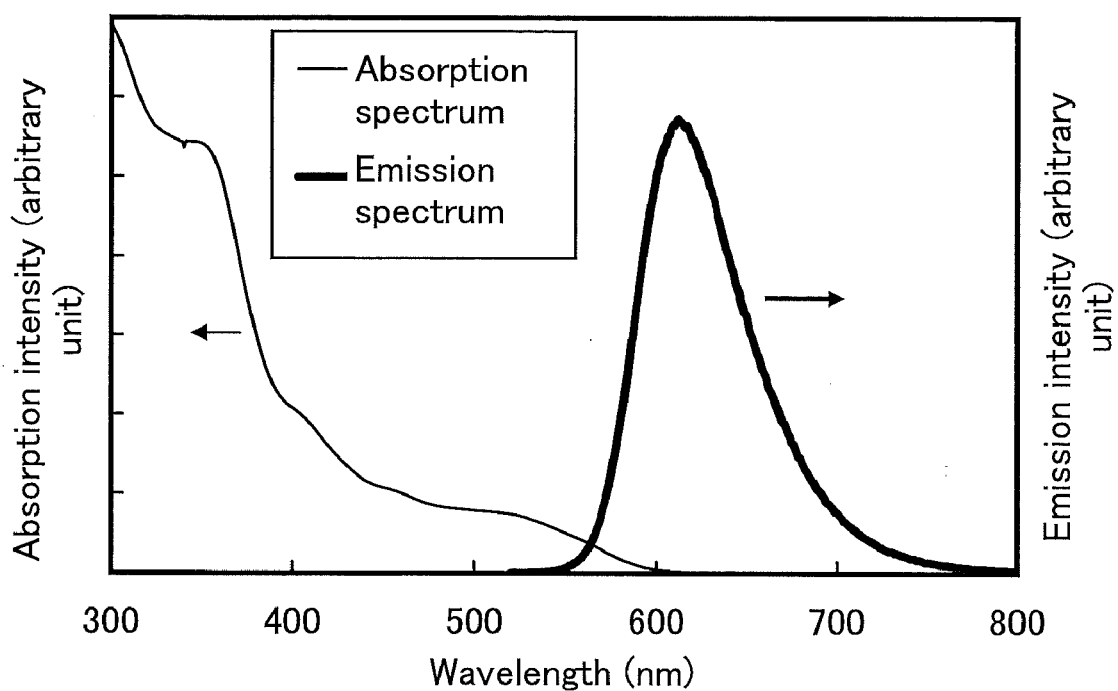
FIG. 6 is a graph showing an absorption spectrum and an emission spectrum of (acetylacetonato)bis[5-(3,5-difluorophenyl)-2,3-diphenylpyrazinato]iridium(III).

Next, an absorption spectrum of [Ir(dppr-3,5FP)₂(acac)] was measured. With the use of an ultraviolet-visible light spectrophotometer (manufactured by Japan Spectroscopy Corporation, V550 type), the absorption spectrum was measured using a dichloromethane solution (0.092 mmol/L) at room temperature. Further, an emission spectrum of [Ir(dppr-3,5FP)₂(acac)] was measured. With the use of a fluorescence spectrophotometer (manufactured by Hamamatsu Photonics Corporation, FS920), the emission spectrum was measured using a degassed dichloromethane solution (0.32 mmol/L) at room temperature. Measurement results are shown in FIG. 6. In FIG. 6, the horizontal axis represents wavelength and the vertical axis represents absorption intensity and emission intensity.

As shown in FIG. 6, the organometallic complex [Ir(dppr-3,5FP)₂(acac)] using Hdppr-3,5FP and the synthesis of which is facilitated by a synthesis method of the present invention has a peak of the light emission at 612 nm and a favorable red light emission was observed from a dichloromethane solution.

This application is based on Japanese Patent Application Serial No. 2008-012468 filed with Japan Patent Office on Jan. 23, 2008, the entire contents of which are hereby incorporated by reference.

What is claimed is:

1. A method for manufacturing a triarylpyrazine derivative represented by a general formula (G1), comprising the step of:

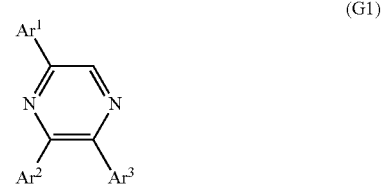

(G1)

irradiating with a microwave a mixture to be reacted, the mixture including a first material represented by a general formula (M1), a second material represented by a general formula (M2), and a dehydrogenation agent,

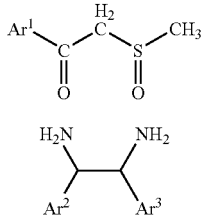
(M1)

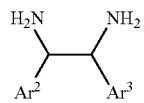
(M2)

wherein $Ar^1$ represents an aryl group having 6 to 14 carbon atoms, which includes at least one electron-withdrawing group, and $Ar^2$ and $Ar^3$ each independently represent a substituted or unsubstituted aryl group having 6 to 14 carbon atoms.

2. The method for manufacturing a triarylpyrazine derivative represented by a general formula (G1), according to claim 1,
wherein the first material is represented by a general formula (M3), and

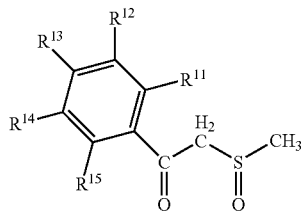
(M3)

wherein $R^{11}$ to $R^{15}$ each independently represent hydrogen or an electron-withdrawing group, and at least one of $R^{11}$ to $R^{15}$ is an electron-withdrawing group.

3. The method for manufacturing a triarylpyrazine derivative represented by a general formula (G1), according to claim 1,
wherein the first material is represented by a general formula (M6), and

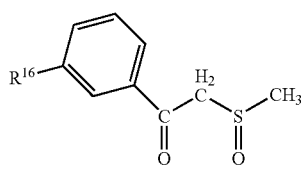
(M6)

wherein $R^{16}$ represents an electron-withdrawing group.

4. The method for manufacturing a triarylpyrazine derivative represented by a general formula (G1), according to claim 1,
wherein the first material is represented by a general formula (M7), and

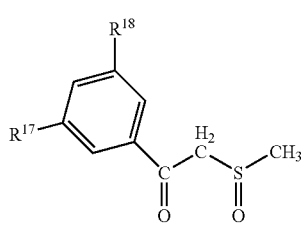
(M7)

wherein $R^{17}$ and $R^{18}$ each independently represent an electron-withdrawing group.

5. The method for manufacturing a triarylpyrazine derivative represented by a general formula (G1), according to claim 1,
wherein the first material is represented by a structural formula (M8):

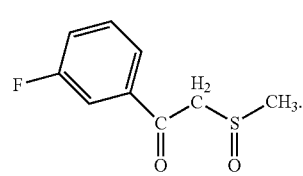
(M8)

6. The method for manufacturing a triarylpyrazine derivative represented by a general formula (G1), according to claim 1,
wherein the first material is represented by a structural formula (M9):

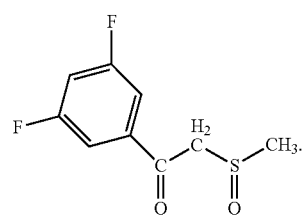
(M9)

7. The method for manufacturing a triarylpyrazine derivative represented by a general formula (G1), according to claim 1, wherein the electron-withdrawing group is any one selected from a group consisting of a halogen group, a haloalkyl group, a cyano group, an alkoxy group, and a nitro group.

8. The method for manufacturing a triarylpyrazine derivative represented by a general formula (G1), according to claim 1, wherein the electron-withdrawing group is any one selected from a group consisting of a fluoro group, a trifluoromethyl group, and a cyano group.

9. The method for manufacturing a triarylpyrazine derivative represented by a general formula (G1), according to claim 1, wherein the mixture including the first material, the second material, and the dehydrogenation agent further includes an organic solvent.

10. The method for manufacturing a triarylpyrazine derivative represented by a general formula (G1), according to claim 9, wherein a dielectric constant of the organic solvent is greater than or equal to 10 and less than or equal to 50.

11. The method for manufacturing a triarylpyrazine derivative represented by a general formula (G1), according to claim 1, wherein the dehydrogenation agent is any one selected from a group consisting of iron(III) chloride, sulfur, sodium hydroxide, and a chloranil-based oxidizer.

12. A method for manufacturing a triarylpyrazine derivative represented by a general formula (G3), comprising the step of:

(G3)

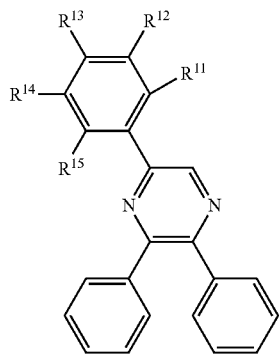

irradiating with a microwave a mixture to be reacted, the mixture including a first material represented by a following general formula (M3), a second material represented by a following structural formula (M5), and a dehydrogenation agent, (M3)

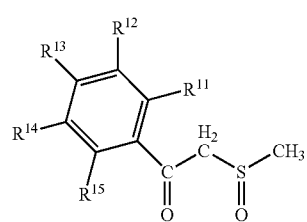

(M5)

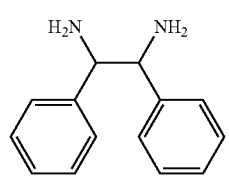

wherein $R^{11}$ to $R^{15}$ each independently represent hydrogen or an electron-withdrawing group, and at least one of $R^{11}$ to $R^{15}$ is an electron-withdrawing group.

13. The method for manufacturing a triarylpyrazine derivative represented by a general formula (G3), according to claim 12,
wherein the first material is represented by a general formula (M6), and (M6)

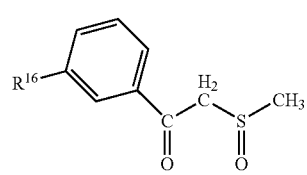

wherein $R^{16}$ represents an electron-withdrawing group.

14. The method for manufacturing a triarylpyrazine derivative represented by a general formula (G3), according to claim 12,
wherein the first material is represented by a general formula (M7), and (M7)

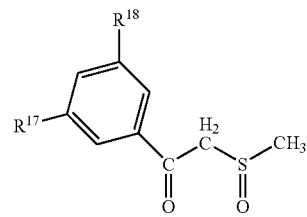

wherein $R^{17}$ and $R^{18}$ each independently represent an electron-withdrawing group.

15. The method for manufacturing a triarylpyrazine derivative represented by a general formula (G3), according to claim 12,
wherein the first material is represented by a structural formula (M8):

(M8)

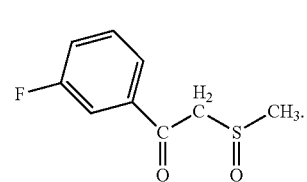

16. The method for manufacturing a triarylpyrazine derivative represented by a general formula (G3), according to claim 12,
wherein the first material is represented by a structural formula (M9):

(M9)

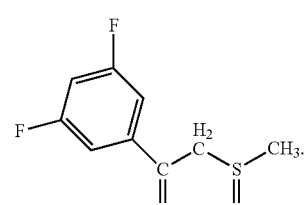

17. The method for manufacturing a triarylpyrazine derivative represented by a general formula (G3), according to claim 12, wherein the electron-withdrawing group is any one selected from a group consisting of a halogen group, a haloalkyl group, a cyano group, an alkoxy group, and a nitro group.

18. The method for manufacturing a triarylpyrazine derivative represented by a general formula (G3), according to claim 12, wherein the electron-withdrawing group is any one selected from a group consisting of a fluoro group, a trifluoromethyl group, and a cyano group.

19. The method for manufacturing a triarylpyrazine derivative represented by a general formula (G3), according to claim 12, wherein the mixture including the first material, the second material, and the dehydrogenation agent further includes an organic solvent.

20. The method for manufacturing a triarylpyrazine derivative represented by a general formula (G3), according to claim 19, wherein a dielectric constant of the organic solvent is greater than or equal to 10 and less than or equal to 50.

21. The method for manufacturing a triarylpyrazine derivative represented by a general formula (G3), according to claim 12, wherein the dehydrogenation agent is any one selected from a group consisting of iron(III) chloride, sulfur, sodium hydroxide, and a chloranil-based oxidizer.

* * * * *